United States Patent
Darrow et al.

(10) Patent No.: US 6,485,957 B1
(45) Date of Patent: Nov. 26, 2002

(54) DNA ENCODING THE HUMAN SERINE PROTEASE EOS

(75) Inventors: Andrew Darrow, Lansdale, PA (US); Jenson Qi, Branchburg, NJ (US); Patricia Andrade-Gordon, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/387,375

(22) Filed: Aug. 31, 1999

Related U.S. Application Data

(63) Continuation-in-part of application No. 09/303,162, filed on Apr. 30, 1999.

(51) Int. Cl.[7] .......................... C12N 9/64; C12N 15/57; C12N 15/62; C12N 15/79; A61K 38/48
(52) U.S. Cl. ..................... 435/226; 435/69.1; 435/69.7; 435/252.3; 435/320.1; 536/23.2; 536/23.4; 514/2
(58) Field of Search ................................ 435/69.1, 226; 415/2

(56) References Cited

U.S. PATENT DOCUMENTS

| | | | |
|---|---|---|---|
| 5,200,340 A | 4/1993 | Forster et al. ............. | 435/69.3 |
| 5,217,878 A | 6/1993 | Van Eekelen et al. ...... | 435/69.1 |
| 5,270,178 A | 12/1993 | Gerlitz et al. .............. | 435/69.1 |
| 5,278,062 A | 1/1994 | Samal et al. ................ | 435/223 |
| 5,326,700 A | 7/1994 | Berg et al. .................. | 435/240 |
| 5,665,566 A | 9/1997 | Lavallie et al. ........... | 424/94.64 |
| 5,763,257 A * | 6/1998 | Bott et al. .................. | 435/221 |
| 5,834,290 A * | 11/1998 | Egelrud et al. ............. | 435/226 |

FOREIGN PATENT DOCUMENTS

| | | | | |
|---|---|---|---|---|
| WO | WO97/47737 | 12/1997 | | |
| WO | WO-98/36054 A1 * | 8/1998 | ............ | C12N/9/12 |
| WO | WO-99/14328 A1 * | 3/1999 | ........... | C12N/15/12 |

OTHER PUBLICATIONS

Davies, B. J., et al., 1996, "Serine proteases in rodent hippocampus", The Journal of Biological Chemistry, vol. 273, pp. 23004–23011.*

Yu, J. X., et al., 1996, "Molecular cloning, tissue-specific expression, and cellular localization of human prostasin mRNA", The Journal of Biological Chemistry, vol. 273, pp. 23004–23011.*

Kühn, Sabine and Zipfel, Peter F., "The Baculovirus Expression Vector pBSV-8His Directs Secretion of Histidine-Tagged Proteins", Gene, 1995, 225–229, vol. 12, Elsevier Science B.V.

Altschul, S. F., Gish, W., Miller, W., Myers, E. W., and Lipman, D. J. (1990). Basic local alignment.

Chen, Z.-L., Yoshida, S., Kato., Momota, Y., Suzuki, J., Tanaka, T., Ito, J., Nishino, H., Aimoto, S., Kiyama, H., and Shiosaka, S. (1995). Expression and activity-dependent changes of a novel limbic-serine protease gene in the hippocampus. J. Neurosci. 15, 5088–97.

(List continued on next page.)

Primary Examiner—Ponnathapu Achutamurthy
Assistant Examiner—William W. Moore
(74) Attorney, Agent, or Firm—John W. Wallen, III

(57) ABSTRACT

Here we describe the molecular identification of a cDNA encoding a novel serine protease we have termed protease EOS. The deduced amino acid sequence, and it alignment with other well-characterized serine proteases indicates that it is a member of the S1 serine protease family. We have found that the protease EOS mRNA is expressed in platelets and leukocytes and more specifically eosinophils. Although this protease is abundantly expressed in ovary, retina and stomach, where it may perform important functions, its expression in platelets and certain cells of the immune system suggests that it may play roles in thrombosis and in the immune process. Enzymatically active protease EOS is amenable to further biochemical analyses for the identification of physiological substrates and specific modulators

5 Claims, 12 Drawing Sheets

```
Amino Acid sequence of EOS protease (SEQ.ID.NO.:7)

Met Arg Gly Val Ser Cys Leu Gln Val Leu Leu Leu
Leu Val Leu Gly Ala Ala Gly Thr Gln Gly Arg Lys
Ser Ala Ala Cys Gly Gln Pro Arg Met Ser Ser Arg
Ile Val Gly Gly Arg Asp Gly Arg Asp Gly Glu Trp
Pro Trp Gln Ala Ser Ile Gln His Pro Gly Ala His
Val Cys Gly Gly Ser Leu Ile Ala Pro Gln Trp Val
Leu Thr Ala Ala His Cys Phe Pro Arg Arg Ala Leu
Pro Ala Glu Tyr Arg Val Arg Leu Gly Ala Leu Arg
Leu Gly Ser Thr Ser Pro Arg Thr Leu Ser Val Pro
Val Arg Arg Val Leu Leu Pro Pro Asp Tyr Ser Glu
Asp Gly Ala Arg Gly Asp Leu Ala Leu Leu Gln Leu
Arg Arg Pro Val Pro Leu Ser Ala Arg Val Gln Pro
Val Cys Leu Pro Val Pro Gly Ala Arg Pro Pro Pro
Gly Thr Pro Cys Arg Val Thr Gly Trp Gly Ser Leu
Arg Pro Gly Val Pro Leu Pro Glu Trp Arg Pro Leu
Gln Gly Val Arg Val Pro Leu Leu Asp Ser Arg Thr
Cys Asp Gly Leu Tyr His Val Gly Ala Asp Val Pro
Gln Ala Glu Arg Ile Val Leu Pro Gly Ser Leu Cys
Ala Gly Tyr Pro Gln Gly His Lys Asp Ala Cys Gln
Gly Asp Ser Gly Gly Pro Leu Thr Cys Leu Gln Ser
Gly Ser Trp Val Leu Val Gly Val Val Ser Trp Gly
Lys Gly Cys Ala Leu Pro Asn Arg Pro Gly Val Tyr
Thr Ser Val Ala Thr Tyr Ser Pro Trp Ile Gln Ala
Arg Val Thr Ser Asn Ala Ser Arg
```

OTHER PUBLICATIONS

Davie, E. W., Fujikawa, K., and Kisiel, W. (1991). The coagulation cascade: initiation, maintenance, and regulation. Biochemistry 30, 10363–70.

Hansson, L., Stroemqvist, M., Baeckman, A., Wallbrandt, P., Carlstein, A., and Egelrud, T. (1994). Cloning, expression, and characterization of stratum corneum chymotryptic enzyme. A skin–specific human serine proteinase. J. Biol. Chem. 269, 19420–6.

Huber, R., and Bode, W. (1978). Structural basis of the activation and action of trypsin. Acc. Chem. Res. 11, 114–22.

Inoue, M., Kanbe, N., Kurosawa, M., and Kido, H. (1998). Cloning and tissue distribution of a novel serine protease esp–1 from human eosinophils. Biochem. Biophys. Res. Commun. 252, 307–312.

Ishii, K., Hein, L., Kobilka, B., and Coughlin, S. R. (1993). Kinetics of thrombin receptor cleavage on intact cells. Relation to signaling. J. Biol. Chem. 268, 9780–6.

Kossiakoff, A. A., Chambers, J. L., Kay, L. M., and Stroud, R. M. (1977). Structure of bovine trypsinogen at 1.9 .ANG. resolution. Biochemistry 16, 654–64.

Kyte, J., and Doolittle, R. F. (1982). A simple method for displaying the hydropathic character of a protein. J. Mol. Biol. 157, 105–32.

Leytus, S. P., Loeb, K. R., Hagen, F. S., Kurachi, K., and Davie, E. W. (1988). A novel trypsin–like serine protease (hepsin) with a putative transmembrane domain expressed by human liver and hepatoma cells. Biochemistry 27, 1067–74.

Little, S. P., Dixon, E. P., Norris, F., Buckley, W., Becker, G. W., Johnson, M., Dobbins, J. R. Wyrick, T., Miller, J. R., Mackellar, W., Hepburn, D., Corvalan, J., Mcclure, D., Liu, X., Stephenson, D., Clemens, J., and Johnstone, E. M. (1997). Zyme, a novel and potentially amyloidogenic enzyme cDNA isolated from Alzheimer's disease brian. J. Biol. Chem. 272, 25135–25142.

Martoglio, B., and Dobberstein, B. (1998). Signal sequences: more than just greasy peptides. Trends Cell Biol. 8, 410–415.

Matthews, B. W., Sigler, P. B., Henderson, R., and Blow, D. M. (1967). Three–dimensional structure of tosyl–.alpha.–chymotrypsin. Nature (London) 214, 652–6.

Nelson, P. S., Gan, L., Ferguson, C., Moss, P., Gelinas, R., Hood, L., and Wang, K. (1999). Molecular cloning and characterization of prostase, an androgen–regulated serine protease with prostate–restricted expression. Proc. Natl. Acad. Sci. U. S. A. 96, 3114–3119.

Pearson, W. R., and Lipman, D. J. (1988). Improved tools for biological sequence comparison. Proc. Natl. Acad. Sci. U. S. A. 85, 2444–8.

Proud, D., and Kaplan, A. P. (1988). Kinin formation: mechanisms and role in inflammatory disorders. Annu. Rev. Immunol. 6, 49–83.

Rawlings, N. D., and Barrett, A. J. (1994). Families of serine peptidases. Methods Enzymol. 244, 19–61.

Reid, K. B. M., and Porter, R. R. (1981). The proteolytic activation systems of complement. Annual Review of Biochemistry 50, 433–464.

Sambroook, J., Fritsch, E. F., and Maniatis, T. (1989). Molecular Cloning: A Laboratory Manual, 2nd ed.: Cold Spring Harbor Laboratory, Cold Spring Harbor, N.Y.

Stroud, R. M., Kay, L. M., and Dickerson, R. E. (1974). Structure of bovine trypsin. Electron density maps of the inhibited enzyme at 5 .ang. and 2.7 .ang. resolution, J. Mol. Biol. 83, 185–208.

Tachias, K., and Madison, E. L. (1996). Converting tissue–type plasminogen activator into a zymogen. J. Bioi. Chem. 271, 28749–28752.

Takayama, T. K., Fujikawa, K., and Davie, E. W. (1997). Characterization of the precursor of prostate–specific antigen Activation by trypsin and by human glandular kallikrein. J. Biol. Chem. 272, 21582–21588.

Wang, Z.–m., Rubin, H., and Schechter, N. M. (1995). Production of active recombinant human chymase from a construct containing the enterokinase cleavage site of trypsinogen in place of the native propeptide sequence Biol. Chem. Hoppe–Seyler 376, 681–4.

Yamashiro, K., Tsuruoka, N., Kodama, S., Tsujimoto, M., Yamamura, Y., Tanaka, T., Nakazato, H., and Yamaguchi, N. (1997). Molecular cloning of a novel trypsin–like serine protease (neurosin) preferentially expressed in brain. Biochim. Biophys. Acta 1350, 11–14.

Yoshida, S., Taniguchi, M., Hirata, A., and Shiosaka, S. (1998). Sequence analysis and expression of human neuropsin cDNA and gene. Gene 213, 9–16.

Yoshida, S., Taniguchi, M., Suemoto, T., Oka, T., He, X., and Shiosaka, S. (1998). cDNA cloning and expression of a novel serine protease, TLSP1. Biochim. Biophys. Acta 1399, 225–228.

Yu, J. X., Chao, L., and Chao, J. (1994). Prostasin is a novel human serine proteinase from seminal fluid. Purification, tissue distribution, and localization in protease gland. J. Biol. Chem. 269, 18843–8.

C. T. N. Pham, D.A. Thomas J.D. Mercer and T. J. Ley Production of Fully Active Recombinant Murine Granzymen B in Yeast The Journal of Biological Chemistry vol. 273, No. 3, Issue of Jan. 16, pp. 1629–1698.

* cited by examiner

FIG. 1A

Nucleotide sequence of EOS (SEQ.ID.NO1)

```
CCACGCGTCCGACCAGAGTCCAAGCCCTAGGCAGTGCCACCCTTACCCAGCCCAGCCTTG
AAGACAGAATGAGAGGGGTTTCCTGTCTCCAGGTCCTGCTCCTTCTGGTGCTGGGAGCTG
CTGGGACTCAGGGAAGGAAGTCTGCAGCCTGCGGGCAGCCCCGCATGTCCAGTCGGATCG
TTGGGGGCCGGGATGGCCGGGACGGAGAGTGGCCGTGGCAGGCGAGCATCCAGCATCCTG
GGGCACACGTGTGCGGGGGTCGCTCATCGCCCCCAGTGGGTGCTGACAGCGGCGCACT
GCTTCCCCAGGAGGGCACTGCCAGCTGAGTACCGCGTGCGCCTGGGGGCGCTGCGTCTGG
GCTCCACCTCGCCCCGCACGCTCTCGGTGCCCGTGCGACGGGTGCTGCTGCCCCCGGACT
ACTCCGAGGACGGGGCCCGCGGCGACCTGGCACTGCTGCAGCTGCGTCGCCCGGTGCCCC
TGAGCGCTCGCGTCCAACCCGTCTGCCTGCCCGTGCCCGGCGCCCGCCCGCCGCCCGGCA
CACCATGCCGGGTCACCGGCTGGGGCAGCCTCCGCCCAGGAGTGCCCCTCCCAGAGTGGC
GACCGCTACAAGGAGTAAGGGTGCCGCTGCTGGACTCGCGCACCTGCGACGGCCTCTACC
ACGTGGGCGCGGACGTGCCCCAGGCTGAGCGCATTGTGCTGCCTGGGAGTCTGTGTGCCG
GCTACCCCCAGGGCCACAAGGACGCCTGCCAGGGTGATTCTGGGGGACCTCTGACCTGCC
TGCAGTCTGGGAGCTGGGTCCTGGTGGGCGTGGTGAGCTGGGCAAGGGTTGTGCCCTGC
CCAACCGTCCAGGGGTCTACACCAGTGTGGCCACATATAGCCCCTGGATTCAGGCTCGCG
TCACTTCTAATGCTAGCCGGTGAGGCTGACCTGGAGCCAGCTGCTGGGGTCCCTCAGCCT
CCTGGTTCATCCAGGCACCTGCCTATACCCCACATCCCTTCTGCCTCGAGGCCAAGATGC
CTAAAAAAGCTAAAGGCCACCCCACCCCCCACCCACCACCTTCTGGCTCCTCTCCTCTTT
GGGGATCACCAGCTCTGACTCCACCAACCCTCATCCAGGAATCTGCCATGAGTCCCAGGG
AGTCACACTCCCCACTCCCTTCCTGGCTTGTATTTACTTTTCTTGGCCCTGGCCAGGGCT
GGGCGCAAGGCACGCAGTGATGGGCAAACCAATTGCTGCCCATCTGGCCTGTGTGCCCAT
CTTTTTCTGGAGAAAGTCAGATTCACAGCATGACAGAGATTTGACACCAGGGAGATCCTC
CATAGCTGGCTTTGAGGACACGGGACCACAGCCATGAGCGGCCTCTAAGAGCTGAGAGA
CAGCCGGCAGGGAATCGGAACCCTCAGACCCACAGCCGCAAGGCACTGGATTCTGGCAGC
ACCCTGAAGGAGCTGGGAAGTAAGTTCTTCCCCAGCCTCCAGATAAGAGCCCCGCCGGCC
AATCCCTTCATTTCAACCTAAAGAGACCCTAAGCAGAGAACCTAGCTGAGCCACTCCTGA
CCTACAAAGTTGTGACTTAATAAATGTGTGCTTTAAGCTGCCAAAAAAAAAAA
```

FIG. 1B

Amino Acid sequence of EOS protease (SEQ.ID.NO.:7)

Met Arg Gly Val Ser Cys Leu Gln Val Leu Leu Leu
Leu Val Leu Gly Ala Ala Gly Thr Gln Gly Arg Lys
Ser Ala Ala Cys Gly Gln Pro Arg Met Ser Ser Arg
Ile Val Gly Gly Arg Asp Gly Arg Asp Gly Glu Trp
Pro Trp Gln Ala Ser Ile Gln His Pro Gly Ala His
Val Cys Gly Gly Ser Leu Ile Ala Pro Gln Trp Val
Leu Thr Ala Ala His Cys Phe Pro Arg Arg Ala Leu
Pro Ala Glu Tyr Arg Val Arg Leu Gly Ala Leu Arg
Leu Gly Ser Thr Ser Pro Arg Thr Leu Ser Val Pro
Val Arg Arg Val Leu Leu Pro Pro Asp Tyr Ser Glu
Asp Gly Ala Arg Gly Asp Leu Ala Leu Leu Gln Leu
Arg Arg Pro Val Pro Leu Ser Ala Arg Val Gln Pro
Val Cys Leu Pro Val Pro Gly Ala Arg Pro Pro Pro
Gly Thr Pro Cys Arg Val Thr Gly Trp Gly Ser Leu
Arg Pro Gly Val Pro Leu Pro Glu Trp Arg Pro Leu
Gln Gly Val Arg Val Pro Leu Leu Asp Ser Arg Thr
Cys Asp Gly Leu Tyr His Val Gly Ala Asp Val Pro
Gln Ala Glu Arg Ile Val Leu Pro Gly Ser Leu Cys
Ala Gly Tyr Pro Gln Gly His Lys Asp Ala Cys Gln
Gly Asp Ser Gly Gly Pro Leu Thr Cys Leu Gln Ser
Gly Ser Trp Val Leu Val Gly Val Val Ser Trp Gly
Lys Gly Cys Ala Leu Pro Asn Arg Pro Gly Val Tyr
Thr Ser Val Ala Thr Tyr Ser Pro Trp Ile Gln Ala
Arg Val Thr Ser Asn Ala Ser Arg

FIG. 4A

```
    Eco RI
    GAATTCACCACCATGGACAGCAAAGGTTCGTCGCAGAAATCCCGCCTGCT
1   ----+----+----+----+----+    50
    CTTAAGTGGTGGTACCTGTCGTTTCCAAGCAGCGTCTTTAGGGCGGACGA
           M  D  S  K  G  S  S  Q  K  S  R  L  L
           └──────── Prolactin Signal Sequence ────────
```

```
    CCTGCTGCTGGTGGTGTCAAATCTACTCTTGTGCCAGGGTGTGGTCTCCG
51  ----+----+----+----+----+    100
    GGACGACGACCACCACAGTTTAGATGAGAACACGGTCCCACACCAGAGGC
     L  L  L  V  V  S  N  L  L  L  C  Q  G  V  V  S
    ──────── Prolactin Signal Sequence ────────
```

```
                                 Not I
    ACTACAAGGACGACGACGACGTGGACGCGGCCGCTCTTGCTGCCCCCTTT
101 ----+----+----+----+----+    150
    TGATGTTCCTGCTGCTGCTGCACCTGCGCCGGCGAGAACGACGGGGGAAA
     D  Y  K  D  D  D  D  V  D  A  A  A  L  A  A  P  F
    ── FLAG ──                          ── EK Pro ──
```

```
                         Xba I
    GATGATGATGACAAGATCGTTGGGGGCTATGCTCTAGAGGACGGAGAGTG
151 ----+----+----+----+----+    200
    CTACTACTACTGTTCTAGCAACCCCCGATACGAGATCTCCTGCCTCTCAC
     D  D  D  D  K  I  V  G  G  Y  A  L  E  D  G  E  W
              ── EK Pro ──
```

FIG. 4B

```
    GCCGTGGCAGGCGAGCATCCAGCATCCTGGGGCACACGTGTGCGGGGGGT
201 -------------------+-------------------+-------------------+-------------------+-------------------+ 250
    CGGCACCGTCCGCTCGTAGGTCGTAGGACCCCGTGTGCACACGCCCCCCA
     P  W  Q  A  S  I  Q  H  P  G  A  H  V  C  G  G
    ─────────────── Protease EOS.CDS ───────────────

CGCTCATCGCCCCCCAGTGGGTGCTGACAGCGGCGCACTGCTTCCCCAGG
251 -------------------+-------------------+-------------------+-------------------+-------------------+ 300
    GCGAGTAGCGGGGGGTCACCCACGACTGTCGCCGCGTGACGAAGGGGTCC
     S  L  I  A  P  Q  W  V  L  T  A  A  H  C  F  P  R
    ─────────────── Protease EOS.CDS ───────────────

AGGGCACTGCCAGCTGAGTACCGCGTGCGCCTGGGGGCGCTGCGTCTGGG
301 -------------------+-------------------+-------------------+-------------------+-------------------+ 350
    TCCCGTGACGGTCGACTCATGGCGCACGCGGACCCCCGCGACGCAGACCC
     R  A  L  P  A  E  Y  R  V  R  L  G  A  L  R  L  G
    ─────────────── Protease EOS.CDS ───────────────

CTCCACCTCGCCCCGCACGCTCTCGGTGCCCGTGCGACGGGTGCTGCTGC
351 -------------------+-------------------+-------------------+-------------------+-------------------+ 400
    GAGGTGGAGCGGGGCGTGCGAGAGCCACGGGCACGCTGCCCACGACGACG
     S  T  S  P  R  T  L  S  V  P  V  R  R  V  L  L
    ─────────────── Protease EOS.CDS ───────────────
```

FIG. 4C

```
       CCCCGGACTACTCCGAGGACGGGGCCCGCGGCGACCTGGCACTGCTGCAG
401  ----------+---------+---------+---------+---------+ 450
       GGGGCCTGATGAGGCTCCTGCCCCGGGCGCCGCTGGACCGTGACGACGTC
        P  P  D  Y  S  E  D  G  A  R  G  D  L  A  L  L  Q
                         ——— Protease EOS.CDS ———
```

```
       CTGCGTCGCCCGGTGCCCCTGAGCGCTCGCGTCCAACCCGTCTGCCTGCC
451  ----------+---------+---------+---------+---------+ 500
       GACGCAGCGGGCCACGGGGACTCGCGAGCGCAGGTTGGGCAGACGGACGG
        L  R  R  P  V  P  L  S  A  R  V  Q  P  V  C  L  P
                         ——— Protease EOS.CDS ———
```

```
       CGTGCCCGGCGCCCGCCCGCCGCCCGGCACACCATGCCGGGTCACCGGCT
501  ----------+---------+---------+---------+---------+ 550
       GCACGGGCCGCGGGCGGGCGGCGGGCCGTGTGGTACGGCCCAGTGGCCGA
        V  P  G  A  R  P  P  P  G  T  P  C  R  V  T  G
                         ——— Protease EOS.CDS ———
```

```
       GGGGCAGCCTCCGCCCAGGAGTGCCCCTCCCAGAGTGGCGACCGCTACAA
551  ----------+---------+---------+---------+---------+ 600
       CCCCGTCGGAGGCGGGTCCTCACGGGGAGGGTCTCACCGCTGGCGATGTT
        W  G  S  L  R  P  G  V  P  L  P  E  W  R  P  L  Q
                         ——— Protease EOS.CDS ———
```

FIG. 4D

```
        GGAGTAAGGGTGCCGCTGCTGGACTCGCGCACCTGCGACGGCCTCTACCA
601     --------+--------+--------+--------+--------+ 650
        CCTCATTCCCACGGCGACGACCTGAGCGCGTGGACGCTGCCGGAGATGGT
         G  V  R  V  P  L  L  D  S  R  T  C  D  G  L  Y  H
        ———————————— Protease EOS.CDS ————————————
```

```
        CGTGGGCGCGGACGTGCCCCAGGCTGAGCGCATTGTGCTGCCTGGGAGTC
651     --------+--------+--------+--------+--------+ 700
        GCACCCGCGCCTGCACGGGGTCCGACTCGCGTAACACGACGGACCCTCAG
         V  G  A  D  V  P  Q  A  E  R  I  V  L  P  G  S
        ———————————— Protease EOS.CDS ————————————
```

```
        TGTGTGCCGGCTACCCCCAGGGCCACAAGGACGCCTGCCAGGGTGATTCT
701     --------+--------+--------+--------+--------+ 750
        ACACACGGCCGATGGGGGTCCCGGTGTTCCTGCGGACGGTCCCACTAAGA
         L  C  A  G  Y  P  Q  G  H  K  D  A  C  Q  G  D  S
        ———————————— Protease EOS.CDS ————————————
```

```
        GGGGGACCTCTGACCTGCCTGCAGTCTGGGAGCTGGGTCCTGGTGGGCGT
751     --------+--------+--------+--------+--------+ 800
        CCCCCTGGAGACTGGACGGACGTCAGACCCTCGACCCAGGACCACCCGCA
         G  G  P  L  T  C  L  Q  S  G  S  W  V  L  V  G  V
        ———————————— Protease EOS.CDS ————————————
```

FIG. 4E

```
    GGTGAGCTGGGGCAAGGGTTGTGCCCTGCCCAACCGTCCAGGGGTCTACA
801 --------+---------+---------+---------+---------+ 850
    CCACTCGACCCCGTTCCCAACACGGGACGGGTTGGCAGGTCCCCAGATGT
     V  S  W  G  K  G  C  A  L  P  N  R  P  G  V  Y
    ─────────────── Protease EOS.CDS ───────────────
```

```
    CCAGTGTGGCCACATATAGCCCCTGGATTCAGGCTCGCGTCACTTCTAAT
851 --------+---------+---------+---------+---------+ 900
    GGTCACACCGGTGTATATCGGGGACCTAAGTCCGAGCGCAGTGAAGATTA
     T  S  V  A  T  Y  S  P  W  I  Q  A  R  V  T  S  N
    ─────────────── Protease EOS.CDS ───────────────
```

```
        Xba I
    GCTTCTAGATACCCCTACGATGTGCCCGATTACGCCGCTAGACATCACCA
901 --------+---------+---------+---------+---------+ 950
    CGAAGATCTATGGGGATGCTACACGGGCTAATGCGGCGATCTGTAGTGGT
     A  S  R  Y  P  Y  D  V  P  D  Y  A  A  R  H  H  H
                  ──────────── HA/HIS-TAG ────────────
```

```
          Not I
    TCACCATCACTAGCGGCCGCTTCCCTTTAGTGAGGGTTAATGCTTCGAGC
951 --------+---------+---------+---------+---------+ 1000
    AGTGGTAGTGATCGCCGGCGAAGGGAAATCACTCCCAATTACGAAGCTCG
      H  H  H  *
```

FIG. 4F

```
      AGACATGATAAGATACATTGATGAGTTTGGACAAACCACAACTAGAATGC
1001 ----------------+----------------+----------------+----------------+----------------+ 1050
      TCTGTACTATTCTATGTAACTACTCAAACCTGTTTGGTGTTGATCTTACG
```
   SV40 Late pA

```
      AGTGAAAAAAATGCTTTATTTGTGAAATTTGTGATGCTATTGCTTTATTT
1051 ----------------+----------------+----------------+----------------+----------------+ 1100
      TCACTTTTTTTACGAAATAAACACTTTAAACACTACGATAACGAAATAAA
```
   SV40 Late pA

```
      GTAACCATTATAAGCTGCAATAAACAAGTT
1101 ----------------+----------------+----------------+ 1130
      CATTGGTAATATTCGACGTTATTTGTTCAA
```

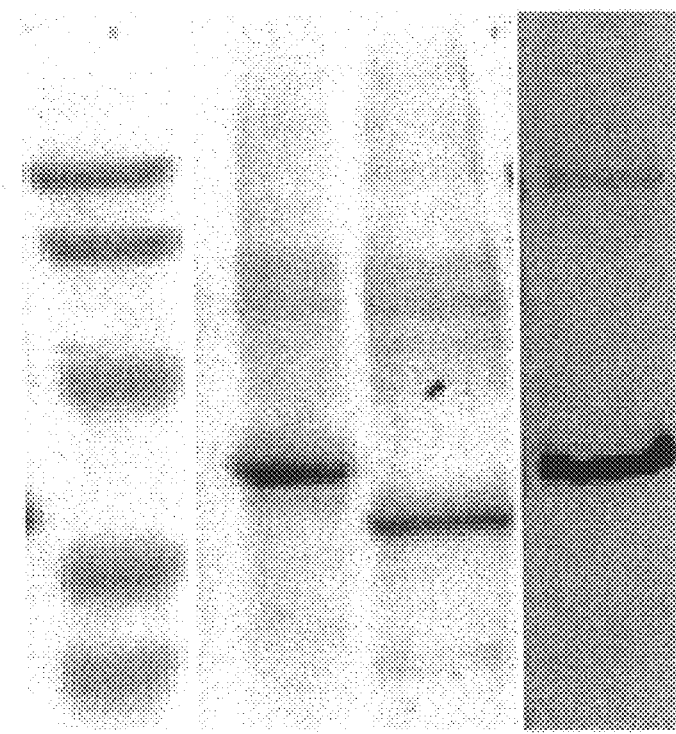

SEQUENCE LISTING

<160> NUMBER OF SEQ ID NOS: 9

<210> SEQ ID NO 1
<211> LENGTH: 1613
<212> TYPE: DNA
<213> ORGANISM: Homo sapiens

<400> SEQUENCE: 1

| | | | | | |
|---|---|---|---|---|---|
| ccacgcgtcc | gaccagagtc | caagccctag | gcagtgccac | ccttacccag | cccagccttg | 60 |
| aagacagaat | gagagggtt | tcctgtctcc | aggtcctgct | ccttctggtg | ctgggagctg | 120 |
| ctgggactca | gggaaggaag | tctgcagcct | gcgggcagcc | ccgcatgtcc | agtcggatcg | 180 |
| ttggggccg | ggatggccgg | gacggagagt | ggccgtggca | ggcgagcatc | cagcatcctg | 240 |
| gggcacacgt | gtgcggggg | tcgctcatcg | ccccccagtg | ggtgctgaca | gcggcgcact | 300 |
| gcttccccag | gagggcactg | ccagctgagt | accgcgtgcg | cctggggcg | ctgcgtctgg | 360 |
| gctccacctc | gccccgcacg | ctctcggtgc | ccgtgcgacg | ggtgctgctg | ccccggact | 420 |
| actccgagga | cggggcccgc | ggcgacctgg | cactgctgca | gctgcgtcgc | ccggtgcccc | 480 |
| tgagcgctcg | cgtccaaccc | gtctgcctgc | ccgtgcccgg | cgcccgcccg | ccgcccggca | 540 |
| caccatgccg | ggtcaccggc | tggggcagcc | tccgcccagg | agtgcccctc | ccagagtggc | 600 |
| gaccgctaca | aggagtaagg | gtgccgctgc | tggactcgcg | cacctgcgac | ggcctctacc | 660 |
| acgtgggcgc | ggacgtgccc | caggctgagc | gcattgtgct | gcctgggagt | ctgtgtgccg | 720 |
| gctaccccca | gggccacaag | gacgcctgcc | agggtgattc | tgggggacct | ctgacctgcc | 780 |
| tgcagtctgg | gagctgggtc | ctggtgggcg | tggtgagctg | gggcaagggt | tgtgccctgc | 840 |
| ccaaccgtcc | aggggtctac | accagtgtgg | ccacatatag | ccctggatt | caggctcgcg | 900 |
| tcacttctaa | tgctagccgg | tgaggctgac | ctggagccag | ctgctggggt | ccctcagcct | 960 |
| cctggttcat | ccaggcacct | gcctatacc | cacatccctt | ctgcctcgag | gccaagatgc | 1020 |
| ctaaaaaagc | taaaggccac | cccacccccc | acccaccacc | ttctggctcc | tctcctcttt | 1080 |
| ggggatcacc | agctctgact | ccaccaaccc | tcatccagga | atctgccatg | agtcccaggg | 1140 |
| agtcacactc | cccactccct | tcctggcttg | tatttactt | tcttggccct | ggccagggct | 1200 |
| gggcgcaagg | cacgcagtga | tgggcaaacc | aattgctgcc | catctggcct | gtgtgcccat | 1260 |
| cttttctgg | agaaagtcag | attcacagca | tgacagagat | ttgacaccag | ggagatcctc | 1320 |
| catagctggc | tttgaggaca | cggggaccac | agccatgagc | ggcctctaag | agctgagaga | 1380 |
| cagccggcag | ggaatcggaa | ccctcagacc | cacagccgca | aggcactgga | ttctggcagc | 1440 |
| accctgaagg | agctgggaag | taagttcttc | cccagcctcc | agataagagc | ccgccggcc | 1500 |
| aatcccttca | tttcaaccta | aagagaccct | aagcagagaa | cctagctgag | ccactcctga | 1560 |
| cctacaaagt | tgtgacttaa | taaatgtgtg | ctttaagctg | ccaaaaaaaa | aaa | 1613 |

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
gagaaagtca gattcacagc                                                     20

-continued

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
ctgcttaggg tctctttagg                                                   20

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
tgagcggcct ttaagagttg agagacagcc ggcagggaat                             40

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
gggatctaga ggacggagag tggccgtggc                                        30

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ctcatctaga agcattagaa gtgacgcgag cctg                                   34

<210> SEQ ID NO 7
<211> LENGTH: 284
<212> TYPE: PRT
<213> ORGANISM: Homo sapiens

<400> SEQUENCE: 7

Met Arg Gly Val Ser Cys Leu Gln Val Leu Leu Leu Val Leu Gly
 1               5                  10                  15

Ala Ala Gly Thr Gln Gly Arg Lys Ser Ala Ala Cys Gly Gln Pro Arg
                20                  25                  30

Met Ser Ser Arg Ile Val Gly Gly Arg Asp Gly Arg Asp Gly Glu Trp
                35                  40                  45

Pro Trp Gln Ala Ser Ile Gln His Pro Gly Ala His Val Cys Gly Gly
        50                  55                  60

Ser Leu Ile Ala Pro Gln Trp Val Leu Thr Ala Ala His Cys Phe Pro
 65                 70                  75                  80

Arg Arg Ala Leu Pro Ala Glu Tyr Arg Val Arg Leu Gly Ala Leu Arg
                85                  90                  95

Leu Gly Ser Thr Ser Pro Arg Thr Leu Ser Val Pro Val Arg Arg Val
```

```
              100                 105                 110
Leu Leu Pro Pro Asp Tyr Ser Glu Asp Gly Ala Arg Gly Asp Leu Ala
        115                 120                 125

Leu Leu Gln Leu Arg Arg Pro Val Pro Leu Ser Ala Arg Val Gln Pro
    130                 135                 140

Val Cys Leu Pro Val Pro Gly Ala Arg Pro Pro Gly Thr Pro Cys
145                 150                 155                 160

Arg Val Thr Gly Trp Gly Ser Leu Arg Pro Gly Val Pro Leu Pro Glu
                165                 170                 175

Trp Arg Pro Leu Gln Gly Val Arg Val Pro Leu Leu Asp Ser Arg Thr
            180                 185                 190

Cys Asp Gly Leu Tyr His Val Gly Ala Asp Val Pro Gln Ala Glu Arg
        195                 200                 205

Ile Val Leu Pro Gly Ser Leu Cys Ala Gly Tyr Pro Gln Gly His Lys
    210                 215                 220

Asp Ala Cys Gln Gly Asp Ser Gly Gly Pro Leu Thr Cys Leu Gln Ser
225                 230                 235                 240

Gly Ser Trp Val Leu Val Gly Val Val Ser Trp Gly Lys Gly Cys Ala
                245                 250                 255

Leu Pro Asn Arg Pro Gly Val Tyr Thr Ser Val Ala Thr Tyr Ser Pro
            260                 265                 270

Trp Ile Gln Ala Arg Val Thr Ser Asn Ala Ser Arg
        275                 280

<210> SEQ ID NO 8
<211> LENGTH: 1130
<212> TYPE: DNA
<213> ORGANISM: Artificial Sequence
<220> FEATURE:
<223> OTHER INFORMATION: Description of Artificial Sequence: Nucleic
      acid sequence of EOS zymogen fusion gene

<400> SEQUENCE: 8
gaattcacca ccatggacag caaaggttcg tcgcagaaat cccgcctgct cctgctgctg      60
gtggtgtcaa atctactctt gtgccagggt gtggtctccg actacaagga cgacgacgac     120
gtggacgcgg ccgctcttgc tgcccccttt gatgatgatg acaagatcgt tgggggctat     180
gctctagagg acggagagtg gccgtggcag gcgagcatcc agcatcctgg ggcacacgtg     240 tgcgggggggt cgctcatcgc ccccagtggg gtgctgacag cggcgcactg cttccccagg     300
agggcactgc cagctgagta ccgcgtgcgc ctggggcgc tgcgtctggg ctccacctcg      360
ccccgcacgc tctcggtgcc cgtgcgacgg gtgctgctgc cccggactac tccgaggac     420 ggggcccgcg gcgacctggc actgctgcag ctgcgtcgcc cggtgcccct gagcgctcgc     480
gtccaacccg tctgcctgcc cgtgcccggc gcccgcccgc cgcccggcac accatgccgg     540
gtcaccggct ggggcagcct ccgcccagga gtgcccctcc cagagtggcg accgctacaa     600
ggagtaaggg tgccgctgct ggactcgcgc acctgcgacg gcctctacca cgtgggcgcg     660
gacgtgcccc aggctgagcg cattgtgctg cctgggagtc tgtgtgccgg ctaccccag      720 ggccacaagg acgcctgcca gggtgattct ggggacctc tgacctgcct gcagtctggg     780
agctgggtcc tggtgggcgt ggtgagctgg ggcaagggtt gtgccctgcc caaccgtcca     840
ggggtctaca ccagtgtggc cacatatagc cctggattc aggctcgcgt cacttctaat     900
gcttctagat acccctacga tgtgcccgat acgccgcta gacatcacca tcaccatcac     960
tagcggccgc ttcccttag tgagggttaa tgcttcgagc agacatgata agatacattg    1020
```

```
atgagtttgg acaaaccaca actagaatgc agtgaaaaaa atgctttatt tgtgaaattt      1080
gtgatgctat tgctttattt gtaaccatta taagctgcaa taaacaagtt               1130
```

<210> SEQ ID NO 9
<211> LENGTH: 316
<212> TYPE: PRT
<213> ORGANISM: Artificial Sequence
<220> FEATURE:
<223> OTHER INFORMATION: Description of Artificial Sequence: Amino acid
      sequence of EOS zymogen fusion gene

<400> SEQUENCE: 9

```
Met Asp Ser Lys Gly Ser Ser Gln Lys Ser Arg Leu Leu Leu Leu
 1               5                  10                  15

Val Val Ser Asn Leu Leu Leu Cys Gln Gly Val Val Ser Asp Tyr Lys
                20                  25                  30

Asp Asp Asp Val Asp Ala Ala Ala Leu Ala Ala Pro Phe Asp Asp
            35                  40                  45

Asp Asp Lys Ile Val Gly Gly Tyr Ala Leu Glu Asp Gly Glu Trp Pro
         50                  55                  60

Trp Gln Ala Ser Ile Gln His Pro Gly Ala His Val Cys Gly Gly Ser
 65                  70                  75                  80

Leu Ile Ala Pro Gln Trp Val Leu Thr Ala Ala His Cys Phe Pro Arg
                 85                  90                  95

Arg Ala Leu Pro Ala Glu Tyr Arg Val Arg Leu Gly Ala Leu Arg Leu
            100                 105                 110

Gly Ser Thr Ser Pro Arg Thr Leu Ser Val Pro Val Arg Arg Val Leu
        115                 120                 125

Leu Pro Pro Asp Tyr Ser Glu Asp Gly Ala Arg Gly Asp Leu Ala Leu
    130                 135                 140

Leu Gln Leu Arg Arg Pro Val Pro Leu Ser Ala Arg Val Gln Pro Val
145                 150                 155                 160

Cys Leu Pro Val Pro Gly Ala Arg Pro Pro Gly Thr Pro Cys Arg
                165                 170                 175

Val Thr Gly Trp Gly Ser Leu Arg Pro Gly Val Pro Leu Pro Glu Trp
            180                 185                 190

Arg Pro Leu Gln Gly Val Arg Val Pro Leu Leu Asp Ser Arg Thr Cys
        195                 200                 205

Asp Gly Leu Tyr His Val Gly Ala Asp Val Pro Gln Ala Glu Arg Ile
    210                 215                 220

Val Leu Pro Gly Ser Leu Cys Ala Gly Tyr Pro Gln Gly His Lys Asp
225                 230                 235                 240

Ala Cys Gln Gly Asp Ser Gly Gly Pro Leu Thr Cys Leu Gln Ser Gly
                245                 250                 255

Ser Trp Val Leu Val Gly Val Val Ser Trp Gly Lys Gly Cys Ala Leu
            260                 265                 270

Pro Asn Arg Pro Gly Val Tyr Thr Ser Val Ala Thr Tyr Ser Pro Trp
        275                 280                 285

Ile Gln Ala Arg Val Thr Ser Asn Ala Ser Arg Tyr Pro Tyr Asp Val
    290                 295                 300

Pro Asp Tyr Ala Ala Arg His His His His His
305                 310                 315
```

DNA ENCODING THE HUMAN SERINE PROTEASE EOS

This application is a continuation-in-part of Ser. No. 09/303,162 filed Mar. 30, 1999.

BACKGROUND OF THE INVENTION

Members of the trypsin/chymotrypsin-like (S1) serine protease family play pivotal roles in a multitude of diverse physiological processes, including digestive processes and regulatory amplification cascades through the proteolytic activation of inactive zymogen precursors. In many instances protease substrates within these cascades are themselves the inactive form, or zymogen, of a "downstream" serine protease. Well-known examples of serine protease-mediated regulation include blood coagulation, (Davie, et al (1991). *Biochemistry* 30:10363–70), kinin formation (Proud and Kaplan (1988). *Ann Rev Immunol* 6: 49–83) and the complement system (Reid and Porter (1981). *Ann Rev Biochemistry* 50:433–464). Although these proteolytic pathways have been known for sometime, it is likely that the discovery of novel serine protease genes and their products will enhance our understanding of regulation within these existing cascades, and lead to the elucidation of entirely novel protease networks.

Differentiated blood cells express an assortment of proteases that are likely to play specific roles in various pathological states. Although granzymes from cytotoxic T cells and natural killer (NK) cells (Smyth et al. (1996). *J. Leukocyte Biol.* 60:555–562), elastase and collagenases from neutrophils (Simon (1993). *Agents Actions Suppl.* 42:27–37) and chymase and tryptase from mast cells (Caughey (1995). *Clin. Allergy Immunol.* 6:305–29; Katunuma and Kido (1988). *J. Cell. Biochem.* 38:291–301) are currently under investigation, their roles in pathophysiological processes are only now being elucidated. In contrast, the proteases from eosinophils have not been characterized and are only currently being molecularly identified. Understanding the physiological roles these eosinophil proteases play will lead to a better understanding of eosinophil function in health and diseased states (Abu-Ghazaleh et al. (1992). *Immunol. Ser.* 57:137–67; Gleich (1996). *Allergol. Int.* 45:35–44; Gleich et al. (1993). *Annu. Rev. Med.* 44:85–101). Proteases are used in non-natural environments for various commercial purposes including laundry detergents, food processing, fabric processing, and skin care products. In laundry detergents, the protease is employed to break down organic, poorly soluble compounds to more soluble forms that can be more easily dissolved in detergent and water. In this capacity the protease acts as a "stain remover." Examples of food processing include tenderizing meats and producing cheese. Proteases are used in fabric processing, for example, to treat wool in order prevent fabric shrinkage. Proteases may be included in skin care products to remove scales on the skin surface that build up due to an imbalance in the rate of desquamation. Common proteases used in some of these applications are derived from prokaryotic or eukaryotic cells that are easily grown for industrial manufacture of their enzymes, for example a common species used is Bacillus as described in U.S. Pat. No. 5,217,878. Alternatively, U.S. Pat. No. 5,278,062 describes serine proteases isolated from a fungus, *Tritirachium album*, for use in laundry detergent compositions. Unfortunately use of some proteases is limited by their potential to cause allergic reactions in sensitive individuals or by reduced efficiency when used in a non-natural environment. It is anticipated that protease proteins derived from non-human sources would be more likely to induce an immune response in a sensitive individual. Because of these limitations, there is a need for alternative proteases that are less immunogenic to sensitive individuals and/or provides efficient proteolytic activity in a non-natural environment. The advent of recombinant technology allows expression of any species' proteins in a host suitable for industrial manufacture.

SUMMARY OF THE INVENTION

Here we describe the molecular identification of a cDNA encoding a novel serine protease we have termed protease EOS. The protease EOS cDNA sequence predicts a pre-proEOS polypeptide of 284 amino acids, and its alignment with other well-characterized serine proteases clearly indicates that it is a member of the S1 serine protease family.

Enzymatically active protease EOS is amenable to further biochemical analyses for the identification of physiological substrates and specific modulators. Modulators identified in the chromogenic assay disclosed herein are potentially useful as therapeutic agents in the treatment of diseases associated with platelet function or elevated eosinophil counts such as in, but not limited to, bronchial asthma and complications arising from hypereosinophilia. In addition, expression of protease EOS in the ovary, retina and stomach suggests that modulators of protease EOS function could be used to treat disorders effecting these tissues. Purified protease EOS can be manufactured as a component for use in commercial products including laundry detergents, stain-removing solutions, and skin care products.

The recombinant DNA molecules coding for EOS, and portions thereof, are useful for isolating homologues of the DNA molecules, identifying and isolating genomic equivalents of the DNA molecules, and identifying, detecting or isolating mutant forms of the DNA molecules

BRIEF DESCRIPTION OF THE DRAWINGS

FIG. 1—The nucleotide (SEQ.ID.NO.::1) and amino acid sequence (SEQ.ID.NO.:7) of the novel protease EOS cDNA is shown.

FIG. 4—The nucleotide and amino acid sequences of the protease EOS catalytic domain in the zymogen activation construct is shown.

FIG. 5—Polyacrylamide gel and Western blot analyses of the recombinant protease PFEK-protease EOS-HA6XHIS. Shown is the polyacrylamide gel containing samples of the novel serine protease PFEK-protease EOS-HA6XHIS stained with Coomassie Brilliant Blue (Leftmost 1, 2.). The relative molecular masses are indicated by the positions of protein standards (M). In the indicated lanes, the purified zymogen was either untreated (−) or digested with EK (+) which was used to cleave and activate the zymogen into its active form. Western blot of the gel, probed with the anti-FLAG MoAb M2, is also shown (rightmost 1). This demonstrates the quantitative cleavage of the expressed and purified zymogen to generate the processed and activated protease.

DETAILED DESCRIPTION

DEFINITIONS

Figure 2:
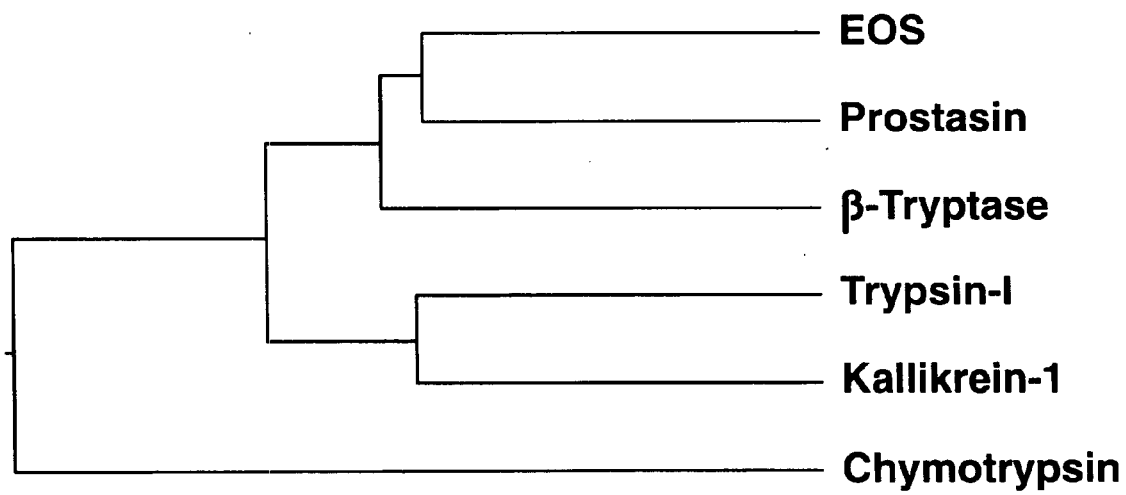
FIG. 2—The phylogenetic tree of the protease EOS amino acid sequence relative to other S1 serine proteases is shown.

The term "protein domain" as used herein refers to a region of a protein that can fold into a stable three-dimensional structure independent to the rest of the protein. This structure may maintain a specific function associated with the domain's function within the protein including enzymatic activity, creation of a recognition motif for another molecule, or provide necessary structural components for a protein to exist in a particular environment. Protein domains are usually evolutionarily conserved regions of proteins, both within a protein superfamily and within other protein superfamilies that perform similar functions.

The term "protein superfamily" as used herein refers to proteins whose evolutionary relationship may not be entirely established or may be distant by accepted phylogenetic standards, but show similar three dimensional structure or display unique consensus of critical amino acids. The term "protein family" as used herein refers to proteins whose evolutionary relationship has been established by accepted phylogenic standards.

The term "fusion protein" as used herein refers to protein constructs that are the result of combining multiple protein domains or linker regions for the purpose of gaining function of the combined functions of the domains or linker regions. This is most often accomplished by molecular cloning of the nucleotide sequences to result in the creation of a new polynucleotide sequence that codes for the desired protein. Alternatively, creation of a fusion protein may be accomplished by chemically joining two proteins together.

The term "linker region" or "linker domain" or similar such descriptive terms as used herein refers to stretches of polynucleotide or polypeptide sequence that are used in the construction of a cloning vector or fusion protein. Functions of a linker region can include introduction of cloning sites into the nucleotide sequence, introduction of a flexible component or space-creating region between two protein domains, or creation of an affinity tag for specific molecule interaction. A linker region may be introduced into a fusion protein without a specific purpose, but results from choices made during cloning.

The term "pre-sequence" as used herein refers to a nucleotide sequence that encodes a secretion signal amino acid sequence. A wide variety of such secretion signal sequences are known to those skilled in the art, and are suitable for use in the present invention. Examples of suitable pre-sequences include, but are not limited to, prolactinFLAG, trypsinogen, and chymoFLAG.

The term "pro-sequence" as used herein refers to a nucleotide sequence that encodes a cleavage site for a restriction protease. A wide variety of cleavage sites for restriction proteases are known to those skilled in the art, and are suitable for use in the present invention. Examples of suitable pro-sequences include, but are not limited to, EK, FXa, and thrombin.

The term "cloning site" or "polycloning site" as used herein refers to a region of the nucleotide sequence contained within a cloning vector or engineered within a fusion protein that has one or more available restriction endonuclease consensus sequences. The use of a correctly chosen restriction endonuclease results in the ability to isolate a desired nucleotide sequence that codes for an in-frame sequence relative to a start codon that yields a desirable protein product after transcription and translation. These nucleotide sequences can then be introduced into other cloning vectors, used create novel fusion proteins, or used to introduce specific site-directed mutations. It is well known by those in the art that cloning sites can be engineered at a desired location by silent mutations, conserved mutation, or introduction of a linker region that contains desired restriction enzyme consensus sequences. It is also well known by those in the art that the precise location of a cloning site can be flexible so long as the desired function of the protein or fragment thereof being cloned is maintained.

The term "tag" as used herein refers to a nucleotide sequence that encodes an amino acid sequence that facilitates isolation, purification or detection of a fusion protein containing the tag. A wide variety of such tags are known to those skilled in the art, and are suitable for use in the present invention. Suitable tags include, but are not limited to, HA-tag, His-tag, biotin, avidin, and antibody binding sites.

As used herein, "expression vectors" are defined herein as DNA sequences that are required for the transcription of cloned copies of genes and the translation of their mRNAs in an appropriate host. Such vectors can be used to express eukaryotic genes in a variety of hosts such as bacteria including *E. coli*, blue-green algae, plant cells, insect cells, fungal cells including yeast cells, and animal cells.

The term "catalytic domain cassette" as used herein refers to a nucleotide sequence that encodes an amino acid sequence encoding at least the catalytic domain of the serine protease of interest. A wide variety of protease catalytic domains may be inserted into the expression vectors of the present invention, including those presently known to those skilled in the art, as well as those not yet having an isolated nucleotide sequence encodes it, once the nucleotide sequence is isolated.

As used herein, a "functional derivative" of the nucleotide sequence, vector, or polypeptide possesses a biological activity (either functional or structural) that is substantially similar to the properties described herein. The term "functional derivatives" is intended to include the "fragments," "variants," "degenerate variants," "analogs" and "homologues" of the nucleotide sequence, vector, or polypeptide. The term "fragment" is meant to refer to any nucleotide sequence, vector, or polypeptide subset of the modules described as pre and pro sequences used for the activation of expressed zymogen precursors. The term "variant" is meant to refer to a nucleotide or amino acid sequence that is substantially similar in structure and function to either the entire nucleic acid sequence or encoded protein or to a fragment thereof. A nucleic acid or amino acid sequence is "substantially similar" to another if both molecules have similar structural characteristics or if both molecules possess similar biological properties. Therefore, if the two molecules possess substantially similar activity, they are considered to be variants even if the structure of one of the molecules is not found in the other or even if the two amino acid sequences are not identical. The term "analog" refers to a protein molecule that is substantially similar in function to another related protein.

Herein we describe a serine protease isolated from eosinophil cells termed EOS. The protease EOS deduced amino acid sequence is most similar to the cloned serine proteases prostasin (Yu et al. (1996). *Genomics* 32:334–40) and tryptase (Miller et al. (1990). *J. Clin. Invest.* 86:864–700). Tryptase, which is produced abundantly in mast cells, has been implicated in asthmatic inflammation and obstruction (Johnson et al. (1997). *Eur. Respir. J.* 10:38–43). Additional homology searches of the Genbank database with the protease EOS nucleotide sequence revealed homology with non-contiguous regions of the human cosmid clone (407D8, Genbank accession # AC005570), which maps to chromosome 16p13.3. Assembly of a continuous nucleic acid sequence from the proposed intron/exon junctions described in the Genbank accession # AC005570 annotation produces a nucleic acid sequence that is shorter and also non-contiguous, and thus substantially different from, protease EOS of the present invention.

Thus, it is likely that the exons delineated in the Genbank accession # AC005570 annotation are incorrect. Therefore, protease EOS of the present invention represents a previously undescribed protease. The use of the previously undescribed sequence of the present invention indicates that chromosome 16p13.3 is the correct the position of the protease EOS gene. Interestingly, the gene encoding prostasin has been localized on chromosome 16p11.2 (Yu et al. (1996). *Genomics* 32:334–40) while several tryptase genes are even clustered within the same chromosome 16p13.3 genomic interval (Pallaoro et al. (1999). *J. Biol. Chem.* 274:3355–3362), and are consequently co-localized with the gene for protease EOS. Recent genetic data links determinants of susceptibility to asthma on chromosome 16 in some populations (Daniels et al. (1996). *Nature* (London) 383:247–253). Eosinophilia, a condition characterized by elevated circulating eosinophils, is associated with numerous allergic states including bronchial asthma (Gleich (1996). *Allergol. Int.* 45:35–44). Therefore protease EOS, or manipulation of this enzyme by chemical modulators, may be useful for treatment of immune processes involving eosinophils, with asthma being one important example.

Proteases are used in non-natural environments for various commercial purposes including laundry detergents, food processing, fabric processing, and skin care products. In laundry detergents, the protease is employed to break down organic, poorly soluble compounds to more soluble forms that can be more easily dissolved in detergent and water. In this capacity the protease acts as a "stain remover." Examples of food processing include tenderizing meats and producing cheese. Proteases are used in fabric processing, for example, to treat wool in order prevent fabric shrinkage. Proteases may be included in skin care products to remove scales on the skin surface that build up due to an imbalance in the rate of desquamation. Unfortunately use of some proteases is limited by their potential to cause allergic reactions in sensitive individuals or by reduced efficiency when used in a non-natural environment. Because of these limitations, there is a need for alternative proteases that are less immunogenic to sensitive individuals and/or provides efficient proteolytic activity in a non-natural environment. Because protease EOS is derived from a human host, it is less likely to induce an allergic reaction in sensitive individuals, and therefore protease EOS may also be useful for formulation of compositions for laundry detergents and skin care products.

The present invention relates to DNA encoding the serine protease EOS that was identified from an eosinophil library, constructed using polyA RNA isolated from pooled diseased eosinophils obtained from allergic asthmatic individuals. The protease EOS as used herein, refers to the encoded protein product which can specifically function as a protease.

The complete amino acid sequence of protease EOS was not previously known, nor was the complete nucleotide sequence encoding protease EOS known. This is the first reported cloning of a full length DNA molecule encoding protease EOS. Based on mRNA distribution, it is predicted that a restricted number of tissues and cell types will contain the described protease. Vertebrate cells capable of producing protease EOS include, but are not limited to eosinophils isolated from blood. Other tissue types may be human spleen, retina, spinal cord and ovary.

Other cells and cell lines may also be suitable for use to isolate the protease EOS cDNA. Selection of suitable cells may be done by screening for protease EOS proteolytic activity in conditioned cell media. Cell types that possess EOS proteolytic activity in this assay may be suitable for the isolation of the protease EOS DNA or mRNA.

Any of a variety of procedures known in the art may be used to molecularly clone protease EOS DNA. These methods include, but are not limited to, direct functional expression of protease genes following the construction of a protease EOS-containing cDNA library in an appropriate expression vector system. Another method is to screen protease EOS-containing cDNA library constructed in a bacteriophage or plasmid shuttle vector with a labeled oligonucleotide probe designed from the amino acid sequence of the protease EOS DNA. An additional method consists of screening a protease EOS-containing cDNA library constructed in a bacteriophage or plasmid shuttle vector with a partial cDNA encoding the protease EOS protein. This partial cDNA is obtained by the specific polymerase chain reaction (PCR) amplification of protease EOS DNA fragments through the design of degenerate oligonucleotide primers from the amino acid sequence of the purified protease EOS protein. Expressed sequence tags (EST)s, identified through homology searching of nucleic acid databases (Altschul et al. (1990). *J. Mol. Biol.* 215:403–10; Pearson and Lipman (1988). *Proc. Natl. Acad. Sci. U. S. A.* 85:2444–8), are also available for this purpose. This particular protease is a member of a multigene family containing highly conserved residues and motifs. Thus, cDNA library screening under reduced stringency to identify related but non-identical homologous cDNAs is possible. More recently, direct PCR using degenerate oligonucleotides of cDNA reverse transcribed from RNA of a given cell type, has been a fruitful approach to isolate novel related cDNAs of interest. Alternatively, the full-length cDNA sequence once published, may be obtained by the specific PCR amplification, through the design of matching oligonucleotide primers flanking the entire coding sequence.

Another method is to isolate RNA from protease EOS-producing cells and translate the RNA into protein via an in vitro or an in vivo translation system. The translation of the RNA into a protein will result in the production of at least a portion of the protease EOS protein that can be identified by, for example, immunological reactivity with an anti-protease EOS antibody. Should the entire catalytic domain be translated, functional proteolytic activity of the EOS protein could conceivably be used to identify RNA fractions containing the protease EOS mRNA. In this method, pools of RNA isolated from protease EOS-producing cells can be analyzed for the presence of an RNA that encodes at least a portion of the EOS protein. Further fractionation of the RNA pool can be done to purify the protease EOS RNA from non-protease EOS RNA. The peptide or protein produced by this method may be analyzed to provide amino acid sequences, which in turn may be used to provide primers for production of protease EOS cDNA. Similarly, RNA used for translation can be analyzed to provide nucleotide sequences and may be used to produce probes for the production of the protease EOS cDNA. This method is known in the art and can be found in, for example, (Maniatis et al. (1989). 1–1626).

It is readily apparent to those skilled in the art that other types of libraries, as well as libraries constructed from other cells or cell types, may be useful for isolating protease EOS-encoding DNA. Other types of libraries include, but are not limited to, cDNA libraries derived from other cells, from non-human organisms, and genomic DNA libraries that include YAC (yeast artificial chromosome) and cosmid libraries.

It is readily apparent to those skilled in the art that suitable cDNA libraries may be prepared from cells or cell lines which have EOS proteolytic activity. The selection of cells or cell lines for use in preparing a cDNA library to isolate the protease EOS cDNA may be done by first measuring cell associated EOS proteolytic activity using the measurement of protease EOS-associated biological activity or a EOS specific immunological reactivity.

Preparation of cDNA libraries can be performed by standard techniques well known in the art. Well known cDNA library construction techniques can be found for example, in (Maniatis et al. (1989). 1–1626).

It is also readily apparent to those skilled in the art that DNA encoding protease EOS may also be isolated from a suitable genomic DNA library. Construction of genomic DNA libraries can be performed by standard techniques well known in the art. Well known genomic DNA library construction techniques can be found in (Maniatis et al. (1989). 1–1626).

In order to clone the protease EOS gene by the above methods, the amino acid sequence of protease EOS may be necessary. To accomplish this, the protease EOS protein may be purified and partial amino acid sequence determined by automated sequencers. It is not necessary to determine the entire amino acid sequence, but the linear sequence of two regions of 6 to 8 amino acids from the protein is determined for the production of primers for PCR amplification of a partial protease EOS DNA fragment. Alternatively, a longer degenerate oligonucleotide probe can be synthesized with a larger consecutive stretch of amino acid sequence determined. This oligonucleotide probe can be labeled and used to screen a suitable cDNA or genomic library, under the appropriate stringency, to isolate DNA corresponding to protease EOS.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the protease EOS sequence, but will be capable of hybridizing to protease EOS DNA even in the presence of DNA oligonucleotides with mismatches. The mismatched DNA oligonucleotides may still sufficiently hybridize to the protease EOS DNA to permit identification and isolation of protease EOS encoding DNA. DNA isolated by these methods can be used to screen DNA libraries from a variety of cell types, from invertebrate and vertebrate sources, and to isolate homologous genes.

Purified biologically active protease EOS may have several different physical forms. Protease EOS may exist as a full-length nascent or unprocessed polypeptide, or as partially processed polypeptides or combinations of processed polypeptides. The full-length nascent protease EOS polypeptide may be posttranslationally modified by specific proteolytic cleavage events, which result in the formation of fragments of the full-length nascent polypeptide. A fragment, or physical association of fragments may have the full biological activity associated with protease EOS however, the degree of protease EOS activity may vary between individual protease EOS fragments and physically associated protease EOS polypeptide fragments.

The cloned protease EOS DNA obtained through the methods described herein may be recombinantly expressed by molecular cloning into an expression vector containing a suitable promoter and other appropriate transcription regulatory elements, and transferred into prokaryotic or eukaryotic host cells to produce recombinant protease EOS protein. Techniques for such manipulations are fully described (Maniatis et al. (1989). 1–1626), and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including $E.\ coli$, blue-green algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant protease EOS in mammalian cells. Commercially available mammalian expression vectors which may be suitable for recombinant protein expression, include but are not limited to, pCI Neo (Promega, Madison, Wis., Madison Wis.), pMAMneo (Clontech, Palo Alto, Calif.), pcDNA3 (InVitrogen, San Diego, Calif.), pMC1neo (Stratagene, La Jolla, Calif.), pXT1 (Stratagene, La Jolla, Calif.), pSG5 (Stratagene, La Jolla, Calif.), EBO-pSV2-neo (ATCC 37593) pBPV-1 (8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

A variety of bacterial expression vectors may be used to express recombinant protease EOS in bacterial cells. Commercially available bacterial expression vectors which may be suitable for recombinant protein expression include, but are not limited to pET vectors (Novagen, Inc., Madison Wis.) and pQE vectors (Qiagen, Valencia, Calif.) pGEX (Pharmacia Biotech Inc., Piscataway, N.J.).

A variety of fungal cell expression vectors may be used to express recombinant protease EOS in fungal cells such as yeast. Commercially available fungal cell expression vectors which may be suitable for recombinant protease EOS expression include but are not limited to pYES2 (InVitrogen, San Diego, Calif.) and Pichia expression vector (InVitrogen, San Diego, Calif.). A variety of insect cell expression systems may be used to express recombinant protease EOS in insect cells. Commercially available baculovirus transfer vectors which may be suitable for the generation of a recombinant baculovirus for recombinant protein expression in Sf9 cells include but are not limited to pFastBacl (Life Technologies, Gaithersberg, Md.) pAcSG2 (Pharmingen, San Diego, Calif.) pBlueBacII (InVitrogen, San Diego, Calif.). In addition, a class of insect cell vectors that permit the expression of recombinant proteins in Drosophila Schneider line 2 (S2) cells is also available (InVitrogen, San Diego, Calif.).

DNA encoding the protease EOS may be subcloned into an expression vector for expression in a recombinant host cell. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to Drosophila S2 (ATCC CRL-1963) and silkworm Sf9 (ATCC CRL-1711), derived cell lines. Cell lines an derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL 1573), The expression vector may be introduced into host cells via any one of a number of techniques including but not limited to transformation, transfection, protoplast fusion, lipofection, and electroporation. The expression vector-containing cells are clonally propagated and individually analyzed to determine whether they produce protease EOS protein. Identification of protease ESO expressing host cell clones may be done by several means, including but not limited to immunological reactivity with anti-protease EOS antibodies, and the presence of host cell-associated EOS proteolytic activity.

Expression of protease EOS DNA may also be performed using in vitro produced synthetic mRNA. Synthetic mRNA or mRNA isolated from protease EOS producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being generally preferred.

To determine the protease EOS DNA sequence(s) that yields optimal levels of EOS proteolytic activity and/or EOS protein, protease EOS DNA molecules including, but not limited to, the following can be constructed: the full-length open reading frame of the protease EOS cDNA encoding the 30-kDa protein from approximately base 69 to approximately base 920 (these numbers correspond to first nucleotide of first methionine and last nucleotide before the first stop codon; FIG. 1) and several constructs containing portions of the cDNA encoding the EOS protease. All constructs can be designed to contain none, all or portions of the 5' or the 3' untranslated region of the protease EOS cDNA. protease EOS activity and levels of protein expression can be determined following the introduction, both singly and in combination, of these constructs into appropriate host cells. Following determination of the protease EOS DNA cassette yielding optimal expression in transient assays, this protease EOS DNA construct is transferred to a variety of expression vectors, for expression in host cells including, but not limited to, mammalian cells, baculovirus-infected insect cells, *E. coli*, and the yeast *S. cerevisiae*.

Host cell transfectants and microinjected oocytes may be used to assay both the levels of protease EOS proteolytic activity and levels of EOS protein by the following methods. In the case of recombinant host cells, this involves the co-transfection of one or possibly two or more plasmids, containing the protease EOS DNA encoding one or more fragments or subunits. In the case of oocytes, this involves the co-injection of synthetic RNAs encoding protease EOS. Following an appropriate period of time to allow for expression, cellular protein is metabolically labeled with, for example $^{35}$S-methionine for 24 hours, after which cell lysates and cell culture supernatants are harvested and subjected to immunoprecipitation with polyclonal antibodies directed against the protease EOS protein.

Other methods for detecting protease EOS expression involve the direct measurement of EOS proteolytic activity in whole cells transfected with protease EOS cDNA or oocytes injected with protease EOS mRNA. Proteolytic activity can be measured by analyzing conditioned media or cell lysates by hydrolysis of a chromogenic or fluorogenic substrate. In the case of recombinant host cells expressing protease EOS, higher levels of substrate hydrolysis would be observed relative to mock transfected cells or cells transfected with expression vector lacking the protease EOS DNA insert. In the case of oocytes, lysates or conditioned media from those injected with RNA encoding protease EOS, would show higher levels of substrate hydrolysis than those oocytes programmed with an irrelevant RNA.

Other methods for detecting proteolytic activity include, but are not limited to, measuring the products of proteolytic degradation of radiolabeled proteins (Coolican et al. (1986). *J. Biol. Chem.* 261:4170–6), fluorometric (Lonergan et al. (1995). *J. Food Sci.* 60:72–3, 78; Twining (1984). *Anal. Biochem.* 143:30–4) or calorimetric (Buroker-Kilgore and Wang (1993). *Anal. Biochem.* 208:387–92) analyses of degraded protein substrates. Zymography following SDS polyacrylamide gel electrophoresis (Wadstroem and Smyth (1973). *Sci. Tools* 20:17–21), as well as by fluorescent resonance energy transfer (FRET)-based methods (Ng and Auld (1989). *Anal. Biochem.* 183:50–6) are also methods used to detect proteolytic activity.

Levels of protease EOS protein in host cells can be quantitated by immunoaffinity. protease EOS-specific affinity beads or protease EOS-specific antibodies are used to isolate for example $^{35}$S-methionine labeled or unlabelled protease EOS protein. Labeled protease EOS protein is analyzed by SDS-PAGE. Unlabelled protease EOS protein is detected by Western blotting, ELISA or RIA assays employing protease EOS specific antibodies.

Because the genetic code is degenerate, more than one codon may be used to encode a particular amino acid, and therefore, the amino acid sequence can be encoded by any of a set of similar DNA oligonucleotides. only one member of the set will be identical to the protease EOS sequence but will be capable of hybridizing to protease EOS DNA even in the presence of DNA oligonucleotides with mismatches under appropriate conditions. Under alternate conditions, the mismatched DNA oligonucleotides may still hybridize to the protease EOS DNA to permit identification and isolation of protease EOS encoding DNA.

DNA encoding protease EOS from a particular organism may be used to isolate and purify homologues of the protease EOS DNA from other organisms. To accomplish this, the first protease EOS DNA may be mixed with a sample containing DNA encoding homologues of protease EOS under appropriate hybridization conditions. The hybridized DNA complex may be isolated and the DNA encoding the homologous DNA may be purified therefrom.

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include, but are not limited to site directed mutagenesis. Examples of altered properties include but are not limited to changes in the affinity of an enzyme for a substrate or a receptor for a ligand.

Several recombinant serine protease purification procedures are available and suitable for use (Hansson et al. (1994). *J. Biol. Chem.* 269:19420–6; Little et al. (1997). *J. Biol. Chem.* 272:25135–25142; Takayama et al. (1997). *J. Biol. Chem.* 272:21582–21588; Yamaoka et al. (1998). *J. Biol. Chem.* 273:11895–11901). As described above for purification of protease EOS from natural sources, recombinant protease EOS may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography. Following expression of protease EOS in a recombinant host cell, as is the case for many members of the S1 serine protease family, protease EOS protein may be recovered as an inactive zymogen precursor form which may require a limited proteolysis to become the proteolytically active.

A major drawback in the expression of full-length serine protease cDNAs for biochemical and enzymological analyses is the overwhelming potential for the production of large amounts of the inactive zymogen. These zymogen precursors often have little or no significant proteolytic activity and thus must be activated by either one of two methods currently available. One method relies on the autoactivation (Little et al. (1997). *J. Biol. Chem.* 272:25135–25142), which may occur in homogeneous purified protease preparations under the correct set of circumstances. Investigators must rigorously evaluate these conditions, which often require high protein concentrations. The second method is the use of a surrogate activating protease, such as trypsin, to cleave the serine protease under investigation, and either inactivate (Takayama et al. (1997). *J. Biol. Chem.* 272:21582–21588) or physically remove (Hansson et al. (1994). *J. Biol. Chem.* 269:19420–6) the contaminating protease following activation. In both methods however, the exact conditions must be established empirically and activating reactions monitored carefully, since inadequate activation or over-digestion leading to degradation and sample loss could always be possible consequences of these activating techniques. Investigators studying particular members of the S1 serine protease family have exploited the use of restriction proteinases on the activation of expressed zymogens in bacteria (Wang et al. (1995). *Biol. Chem. Hoppe-Seyler* 376:681–4) and mammalian cells (Yamashiro et al. (1997). *Biochim. Biophys. Acta* 1350:11–14). In one report, the authors successfully engineered the secretion of proteolytically processed and activated murine granzyme B by taking advantage of the endogenous yeast KEX2 signal peptidase in a *Pichia pastoris* expression system (Pham et al. (1998). *J. Biol. Chem.* 273:1629–1633). Another aspect of the present invention provides a fusion gene comprising protease EOS that encodes a protease EOS that facilitates activation of the protease.

DNA clones, including protease EOS DNA, are identified which encode proteins that, when expressed in a recombinant host, produce protein with the amino acid sequence of protease EOS, which may or may not possess a prdteolytic activity. The expression of protease EOS DNA results in the reconstitution of the properties observed in oocytes injected with protease EOS-encoding poly $(A)^+$ RNA.

Recombinant protease EOS can be separated from other cellular proteins by use of an immunoaffinity column made with monoclonal or polyclonal antibodies specific for full-length nascent protease EOS polypeptide fragments of protease EOS. Monospecific antibodies to protease EOS are purified from mammalian antisera containing antibodies reactive against protease EOS or are prepared as monoclonal antibodies reactive with protease EOS using the technique of (Kohler and Milstein (1976). *Eur J Immunol* 6:511–9). Monospecific antibody as used herein is defined as a single antibody species or multiple antibody species with homogenous binding characteristics for protease EOS. Homogenous binding as used herein refers to the ability of the antibody species to bind to a specific antigen or epitope, such as those associated with the protease EOS, as described above. Protease EOS specific antibodies are raised by immunizing animals such as mice, rats, guinea pigs, rabbits, goats, horses and the like, with rabbits being preferred, with an appropriate concentration of protease EOS either with or without an immune adjuvant.

Preimmune serum is collected prior to the first immunization. Each animal receives between about 0.1 mg and about 1000 mg of protease EOS protein or peptide(s), derived from the deduced protease EOS DNA sequence or perhaps by the chemical degradation or enzymatic digestion of the protease EOS protein itself, associated with an acceptable immune adjuvant. Such acceptable adjuvants include, but are not limited to, Freund's complete, Freund's incomplete, alum-precipitate, water in oil emulsion containing *Corynebacterium parvum* and tRNA, or Titermax (CytRx, Norcross, Ga.). The initial immunization consists of protease EOS antigen in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (MoAb) reactive with protease EOS are prepared by immunizing inbred mice, preferably Balb/c, with protease EOS protein or peptide(s), derived from the deduced protease EOS DNA sequence or perhaps by the chemical degradation or enzymatic digestion of the protease EOS protein itself. The mice are immunized by the IP or SC route with about 0.1 mg to about 10 mg, preferably about 1 mg, of protease EOS antigen in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of protease EOS antigen in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp 2/0, with Sp 2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using protease EOS or antigenic peptide(s) as the antigen. The culture fluids are also tested in the Ouchterlony precipitation assay to determine the isotype of the MoAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-protease EOS MoAb is carried out by growing the hybridoma in DMEM containing about 2% fetal calf serum to obtain sufficient quantities of the specific MoAb. The monoclonal antibodies are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of protease EOS in body fluids or tissue and cell extracts.

It is readily apparent to those skilled in the art that the above described methods for producing monospecific antibodies may be utilized to produce antibodies specific for protease EOS polypeptide fragments, or full-length nascent protease EOS polypeptide. Specifically, it is readily apparent to those skilled in the art that monospecific antibodies may be generated which are specific for only one or more protease EOS epitopes.

Protease EOS antibody affinity columns are made by adding the antibodies to Affigel-10 (Bio-Rad), a gel support which is activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing protease EOS are slowly passed through the column. The column is then washed with phosphate buffered saline until the optical density ($A_{280}$) falls to background, then the protein is eluted with 0.23 M glycine-HCl (pH 2.6). The purified protease EOS protein is then dialyzed against phosphate buffered saline.

Protease EOS mRNA is expressed in retina, ovary, and stomach, where the encoded protease EOS protein may perform important functions during normal physiology, and possibly pathological states. Thus, modulators of protease EOS function could be used to treat disorders effecting these tissues. We have also found that the protease EOS mRNA is expressed human platelets, and spleen which is a major site of blood cell metabolism, as well as in leukocytes and more specifically in eosinophils. Eosinophilia, is a condition characterized by elevated circulating eosinophils, and is associated with numerous allergic states including bronchial asthma (Gleich (1996). *Allergol. Int.* 45:35–44). Thus, protease EOS expression in platelets and certain cells of the immune system suggests that it may play roles in hemostasis and a subset of immune processes. Modulators of protease EOS function could therefore potentially be used to treat disorders in hemostasis and/or to moderate particular immune responses.

The present invention is also directed to methods for screening for compounds that modulate the expression of DNA or RNA encoding protease T as well as the function of protease T protein in vivo. Compounds that modulate these activities may be DNA, RNA, peptides, proteins, or non-proteinaceous organic molecules. Compounds may modulate by increasing or attenuating the expression of DNA or RNA encoding protease T, or the function of protease T protein. Compounds that modulate the expression of DNA or RNA encoding protease T or the function of protease T protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are potentially useful as therapeutic agents. Methods for detecting compounds that modulate protease T proteolytic activity comprise combining compound, protease T and a suitable labeled substrate and monitoring an effect of the compound on the protease by changes in the around of substrate as a function of time. Labeled substrates include, but are. not limited to, substrate that are radiolabeled (Coolican et al. (1986). *J. Biol. Chem.* 261:4170–6), fluorometric (Lonergan et al. (1995). *J. Food Sci.* 60:72–3, 78; Twining (1984). *Anal. Biochem.* 143:30–4) or calorimetric (Buroker-Kilgore and Wang (1993). *Anal. Biochem.* 208:387–92). Zymography following SDS polyacrylamide gel electrophoresis (Wadstroem and Smyth (1973). *Sci. Tools* 20:17–21), as well as by fluorescent resonance energy transfer (FRET)-based methods (Ng and Auld (1989). *Anal. Biochem.* 183:50–6) are also methods used to detect compounds that modulate protease T proteolytic activity. Compounds that are agonists will increase the rate of substrate degradation and will result in less remaining substrate as a function of time. Compounds that are antagonists will decrease the rate of substrate degradation and will result in greater remaining substrate as a function of time.

Kits containing protease EOS DNA or RNA, antibodies to protease EOS, or protease EOS protein may be prepared. Such kits are used to detect DNA that hybridizes to protease EOS DNA or to detect the presence of protease EOS protein or peptide fragments in a sample. Such characterization is useful for a variety of purposes including but not limited to forensic analyses, diagnostic applications, and epidemiological studies.

The present invention is also directed to methods for screening for compounds that modulate the expression of DNA or RNA encoding protease EOS as well as the function of protease EOS protein in vivo. Compounds that modulate these activities may be DNA, RNA, peptides, proteins, or non-proteinaceous organic molecules. Compounds may modulate by increasing or attenuating the expression of DNA or RNA encoding protease EOS, or the function of protease EOS protein. Compounds that modulate the expression of DNA or RNA encoding protease EOS or the function of protease EOS protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are potentially useful as therapeutic agents. Methods for detecting compounds that modulate protease EOS proteolytic activity comprise combining compound, protease EOS and a suitable labeled substrate and monitoring an effect of the compound on the protease by changes in the amount of substrate as a function of time. Labeled substrates include, but are not limited to, substrates that are radiolabeled (Coolican et al. (1986). *J. Biol. Chem.* 261:4170–6), fluorometric (Lonergan et al. (1995). *J. Food Sci.* 60:72–3, 78; Twining (1984). *Anal. Biochem.* 143:30–4) or calorimetric (Buroker-Kilgore and Wang (1993). *Anal. Biochem.* 208:387–92). Zymography following SDS polyacrylamide gel electrophoresis (Wadstroem and Smyth (1973). *Sci. Tools* 20:17–21), as well as by fluorescent resonance energy transfer (FRET)-based methods (Ng and Auld (1989). *Anal. Biochem.* 183:50–6) are also methods used to detect compounds that modulate protease EOS proteolytic activity. Compounds that are agonists will increase the rate of substrate degradation and will result in less remaining substrate as a function of time. Compounds that are antagonists will decrease the rate of substrate degradation and will result in greater remaining substrate as a function of time.

Nucleotide sequences that are complementary to the protease EOS encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other protease EOS antisense oligonucleotide mimetics. protease EOS antisense molecules may be introduced into cells by microinjection, liposome encapsulation or by expression from vectors harboring the antisense sequence. protease EOS antisense therapy may be particularly useful for the treatment of diseases where it is beneficial to reduce protease EOS expression or activity.

Protease EOS gene therapy may be used to introduce protease EOS into the cells of target organisms. The protease EOS gene can be ligated into viral vectors that mediate transfer of the protease EOS DNA by infection of recipient host cells. Suitable viral vectors include retrovirus, adenovirus, adeno-associated virus, herpes virus, vaccinia virus, poliovirus and the like. Alternatively, protease EOS DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo protease EOS gene therapy. Protease EOS gene therapy may be particularly useful for the treatment of diseases where it is beneficial to elevate protease EOS expression or activity.

Pharmaceutically useful compositions comprising protease EOS DNA, protease EOS RNA, or protease EOS protein, or modulators of protease EOS activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of protease EOS-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the protease EOS activity while minimizing any potential toxicity. In addition, co-administration or sequential administration of other agents may be desirable.

The protease EOS may be formulated as an active ingredient in non-pharmaceutical commercial products including laundry detergents, skin care lotions or creams. In these formulations the protease EOS is utilized to degrade proteins to increase the efficacy of the product. For example, in laundry detergent formulations inclusion of the protease EOS would act as a "stain remover" by degrading proteacious contaminants from fabric such that the organic compound would become more soluble in detergent and water. Protease EOS can be included in skin care products to aid in desquamation, the process of elimination of the superficial layers of the stratum corneum. An additional benefit of utilizing the protease EOS in non-pharmaceutical commercial formulations is that it is not likely to induce allergic response in sensitive individuals since the protease EOS is of human origin.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of protease EOS activity can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a protease EOS modulating agent.

The daily dosage of the products may be varied over a wide range from 0.01 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the protease EOS modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage-may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that may be employed include glycerin and the like. For parenteral administration, sterile suspensions and solutions are desired. Isotonic preparations, which generally contain suitable preservatives, are employed when intravenous administration is desired.

Topical preparations containing the active drug component can be admixed with a variety of carrier materials well known in the art, such as, eg., alcohols, aloe vera gel, allantoin, glycerine, vitamin A and E oils, mineral oil, PPG2 myristyl propionate, and the like, to form, eg., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cottonseed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators. Proteases are used in non-natural environments for various commercial purposes including laundry detergents, food processing, fabric processing, and skin care products. In laundry detergents, the protease is employed to break down organic, poorly soluble compounds to more soluble forms that can be more easily dissolved in detergent and water. In this capacity the protease acts as a "stain remover." Examples of food processing include tenderizing meats and producing cheese. Proteases are used in fabric processing, for example, to treat wool in order prevent fabric shrinkage. Proteases may be included in skin care products to remove scales on the skin surface that build up due to an imbalance in the rate of desquamation. Common proteases used in some of these applications are derived from prokaryotic or eukaryotic cells that are easily grown for industrial manufacture of their enzymes, for example a common species used is Bacillus as described in U.S. Pat. No. 5,217,878. Alternatively, U.S. Pat. No. 5,278,062 describes serine proteases isolated from a fungus, *Tritirachium album*, for use in laundry detergent compositions. Unfortunately use of some proteases is limited by their potential to cause allergic reactions in sensitive individuals or by reduced efficiency when used in a non-natural environment. It is anticipated that protease proteins derived from non-human sources would be more likely to induce an immune response in a sensitive individual. Because of these limitations, there is a need for alternative proteases that are less immunogenic to sensitive individuals and/or provides efficient proteolytic activity in a non-natural environment. The advent of recombinant technology allows expression of any species' proteins in a host suitable for industrial manufacture.

Another aspect of the present invention relates to compositions comprising the protease EOS and an acceptable carrier. The composition may be any variety of compositions that requires a protease component. Particularly preferred are compositions that may come in contact with humans, for example, through use or manufacture. The use of the protease EOS of the present invention is believed to reduce or eliminate the immunogenic response users and/or handlers might otherwise experience with a similar composition containing a known protease, particularly a protease of non-human origin. Preferred compositions are skin care compositions and laundry detergent compositions.

Herein, "acceptable carriers" includes, but is not limited to, cosmetically-acceptable carriers, pharmaceutically-acceptable carriers, and carriers acceptable for use in cleaning compositions.

Skin Care Compositions

Skin care compositions of the present invention preferably comprise, in addition to the protease EOS, a cosmetically- or pharmaceutically-acceptable carrier.

Herein, "cosmetically-acceptable carrier" means one or more compatible solid or liquid filler diluents or encapsulating substances which are suitable for use in contact with the skin of humans and lower animals without undue toxicity, incompatibility, instability, irritation, allergic response, and the like, commensurate with a reasonable benefit/risk ratio.

Herein, "pharmaceutically-acceptable" means one or more compatible drugs, medicaments or inert ingredients which are suitable for use in contact with the tissues of humans and lower animals without undue toxicity, incompatibility, instability, irritation, allergic response, and the like, commensurate with a reasonable. benefit/risk ratio. Pharmaceutically-acceptable carriers must, of course, be of sufficiently high purity and sufficiently low toxicity to render them suitable for administration to the mammal being treated.

Herein, "compatible" means that the components of the cosmetic or pharmaceutical compositions are capable of being commingled with the protease EOS, and with each other, in a manner such that there is no interaction which would substantially reduce the cosmetic or pharmaceutical efficacy of the composition under ordinary use situations.

Preferably the skin care compositions of the present invention are topical compositions, i.e., they are applied topically by the direct laying on or spreading of the composition on skin. Preferably such topical compositions comprise a cosmetically- or pharmaceutically-acceptable topical carrier.

The topical composition may be made into a wide variety of product types. These include, but are not limited to, lotions, creams, beach oils, gels, sticks, sprays, ointments, pastes, mousses, and cosmetics; hair care compositions such as shampoos and conditioners (for, e.g., treating/preventing dandruff); and personal cleansing compositions. These product types may comprise several carrier systems including, but not limited to, solutions, emulsions, gels and solids.

Preferably the carrier is a cosmetically- or pharmaceutically-acceptable aqueous or organic solvent. Water is a preferred solvent. Examples of suitable organic solvents include: propylene glycol, polyethylene glycol (200–600), polypropylene glycol (425–2025), propylene glycol-14 butyl ether, glycerol, 1,2,4butanetriol, sorbitol esters, 1,2,6-hexanetriol, ethanol, isopropanol, butanediol, and mixtures thereof. Such solutions useful in the present invention preferably contain from about 0.001% to about 25% of the protease EOS, more preferably from about 0.1% to about 10% more preferably from about 0.5% to about 5%; and preferably from about 50% to about 99.99% of an acceptable aqueous or organic solvent, more preferably from about 90% to about 99%.

Skin care compositions of the present invention may further include a wide variety of additional oil-soluble materials and/or water-soluble materials conventionally used in topical compositions, at their art-established levels. Such additional components include, but are not limited to: thickeners, pigments, fragrances, humectants, proteins and polypeptides, preservatives, pacifiers, penetration enhancing agents, collagen, hylauronic acid, elastin, hydrolysates, primrose oil, jojoba oil, epidermal growth factor, soybean saponins, mucopolysaccharides, Vitamin A and derivatives thereof, Vitamin B2, biotin, pantothenic acid, Vitamin D, and mixtures thereof.

Cleaning Compositions

Cleaning compositions of the present invention preferably comprise, in addition to the protease EOS, a surfactant. The cleaning composition may be in a wide variety of forms, including, but not limited to, hard surface cleaning compositions, dishcare cleaning compositions, and laundry detergent compositions.

Preferred cleaning compositions are laundry detergent compositions. Such laundry detergent compositions include, but not limited to, granular, liquid and bar compositions. Preferably, the laundry detergent composition further comprises a builder.

The laundry detergent composition of the present invention contains the protease EOS at a level sufficient to provide a "cleaning-effective amount". The term "cleaning effective amount" refers to any amount capable of producing a cleaning, stain removal, soil removal, whitening, deodorizing, or freshness improving effect on substrates such as fabrics, dishware and the like. In practical terms for current commercial preparations, typical amounts are up to about 5 mg by weight, more typically 0.01 mg to 3 mg, of active enzyme per gram of the detergent composition. Stated another way, the laundry detergent compositions herein will typically comprise from 0.001% to 5%, preferably 0.01%–3%, more preferably 0.01% to 1% by weight of raw protease EOS preparation. Herein, "raw protease EOS preparation" refers to preparations or compositions in which the protease EOS is contained in prior to its addition to the laundry detergent composition. Preferably, the protease BOS is present in such raw protease EOS preparations at levels sufficient to provide from 0.005 to 0.1 Anson units (AU) of activity per gram of raw protease EOS preparation. For certain detergents, such as in automatic dishwashing, it maybe desirable to increase the active protease EOS content of the raw protease EOS preparation in order to minimize the total amount of non-catalytically active materials and thereby improve spotting/filming or other end-results. Higher active levels may also be desirable in highly concentrated detergent formulations.

Preferably, the laundry detergent compositions of the present invention, including but not limited to liquid compositions, may comprise from about 0.001% to about 10%, preferably from about 0.005% to about 8%, most preferably from about 0.01% to about 6%, by weight of an enzyme stabilizing system. The enzyme stabilizing system can be any stabilizing system that is compatible with the protease EOS, or any other additional detersive enzymes that may be included in the composition. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

The detergent composition also comprises a detersive surfactant. Preferably the detergent composition comprises at least about 0.01% of a detersive surfactant; more preferably at least about 0.1%; more preferably at least about 1%; more preferably still, from about 1% to about 55%.

Preferred detersive surfactants are cationic, anionic, nonionic, ampholytic, zwifterionic, and mixtures thereof, further described herein below. Nonlimiting examples of detersive surfactants useful in the detergent composition include, the conventional C11–C18 alkyl benzene sulfonates ("LAS") and primary, branched-chain and random C10–C20 alkyl sulfates ("AS"), the C10–C18 secondary (2,3) alkyl sulfates of the formula $CH_3(CH_2)x(CHOSO_3-M+)$ $CH_3$ and $CH_3 (CH_2)y(CHOSO_3-M+) CH_2CH_3$ where x and (y+1) are integers of at least about 7, preferably at least about 9, and M is a water-solubilizing cation, especially sodium, unsaturated sulfates such as oleyl sulfate, the C10–C18 alkyl alkoxy sulfates ("AExS"; especially EO 1–7 ethoxy sulfates), C10–C18 alkyl alkoxy carboxylates (especially the EO 1–5 ethoxycarboxylates), the C10–18 glycerol ethers, the C10–C18 alkyl polyglycosides and their corresponding sulfated polyglycosides, and C12–C18 alpha-sulfonated fatty acid esters. If desired, the conventional nonionic and amphoteric surfactants such as the C12–C18 alkyl ethoxylates ("AE") including the so-called narrow peaked alkyl Ethoxylates and C6–C12 alkyl phenol alkoxylates (especially ethoxylates and mixed ethoxy/propoxy), C12–C18 betaines and solfobetaines ("sultaines"), C10–C18 amine oxides, and the like, can also be included in the overall compositions. The C10–C18 N-alkyl polyhydroxy fatty acid amides can also be used. Typical examples include the C12–C18 N-methylglucamides. See WO 9,206,154. Other sugar-derived surfactants include the N-alkoxy polyhydroxy fatty acid amides, such as C10–C18 N-(3-methoxypropyl) glucamide. The N-propyl through N-hexyl C12–C18 glucamides can be used for low sudsing. C10–C20 conventional soaps may also be used. If high sudsing is desired, the branched-chain C10–C16 soaps may be used. Mixtures of anionic and nonionic surfactants are especially useful. Other conventional useful surfactants are listed in standard texts. Detergent builders are also included in the laundry detergent composition to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a SiO2:Na2O ration in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6") Unlike zeolite builders, the Na SKS-6 silicate builder does not contain aluminum. NaSKS-6 has the delta-Na2SiO5 morphology form of layered silicate. It can be prepared by methods such as those described in German DE-A-3,417,649 and DE-A-3,742,043. SKS-6 is a highly preferred layered silicate for use herein, but other such layered silicates, such as those having the general formula NaMSixO2x+1 yH20 wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-1 1, as the alpha, beta and gamma forms. As noted above, the delta-Na2SiO5 (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

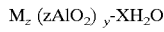

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (b), Zeolite MAP and Zeolite X. In an especially preferred embodiment, the crystalline aluminosilicate ion exchange material has the formula:

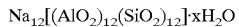

wherein x is from about 20 to about 30, especially about 27. This material is known as Zeolite A. Dehydrated zeolites (x=0–10) may also be used herein. Preferably, the alumino-silicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of poiycarboxylate builders encompasses the ether polycarboxylates, including oxydisuccinate, as disclosed in Berg, U.S. Pat. No. 3,128,287, issued Apr. 7, 1964, and Lamberti et al., U.S. Pat. No. 3,635,830, issued Jan. 18, 1972. See also "TMSFTDS" builders of U.S. Pat. No. 4,663,071, issued to Bush et al., on May 5, 1987. Suitable ether polycarboxylates also include cyclic compounds, particularly alicyclic compounds, such as those described in U.S. Pat. Nos. 3,923,679 to Rapko, issued Dec. 2, 1975; 3,835,163 to Rapko, issued Sep. 10, 1974; 4,158,635 to Crutchfield et al., issued Jun. 19, 1979; 4,120,874 to Crutchfield et al., issued Oct. 17, 1978; and 4,102,903 to Crutchfield et al., issued Jul. 25, 1978.

Other useful detergency builders include the ether hydroxypolycarboxylates, copolymers of maleic anhydride with ethylene or vinyl methyl ether, 1, 3, 5-trihydroxy benzene-2, 4, 6-t6sulphonic acid, and carboxymethyloxysuccinic acid, the various alkali metal, ammonium and substituted ammonium salts of polyacetic acids such as. ethylenediamine tetraacetic acid and nitrilotriacetic acid, as well as polycarboxylates such as Mellitic acid, succinic acid, oxydisuccinic acid, polymaleic acid, benzene 1,3,5-tricarboxylic acid, carboxymethyloxysuccinic acid, and soluble salts thereof, citrate builders, e.g., citric acid and soluble salts thereof (particularly sodium salt), are polycarboxylate builders of particular importance for heavy-duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984 to Bush, issued Jan. 28, 1986. Useful succinic acid builders include the C5–C20 alkyl and alkenyl succinic acids and salts thereof. A particularly preferred compound of this type is dodecenylsuccinic acid. Specific examples of succinate builders include: laurylsuccinate, myristylsuccinate, paimitylsuccinate, 2-dodecenylsuccinate (preferred), 2pentadecenylsuccinate, and the like. Lauryisuccinates are the preferred builders of this group, and are described in European Patent Application 200,263 to Barrat et al., published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also U.S. Pat. No. 3,723,322 to Diehl, issued Mar. 27, 1973.

Fatty acids, e.g., C12–C18 monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-l,l-diphosphonate and other known phosphonates (see, for example, U.S. Pat. Nos. 3,159,581 to Diehl, issued Dec. 1, 1964; 3,213,030 to Diehl, issued Oct. 19, 1965; 3,400,148 to Quimby, issued Sep. 3, 1968; 3,422,021 to Roy, issued Jan. 14, 1969; and 3,422,137 to Quimby, issued Jan. 4, 1969) can also be used. Additional components which may be used in the laundry detergent compositions of the present invention include, but are not limited to: alkoxylated polycarboxylates (to provide, e.g., additional grease stain removal performance), bleaching agents, bleach activators, bleach catalysts, brighteners, chelating agents, clay soil removal/anti-redeposition agents, dye transfer inhibiting agents, additional enzymes (including lipases, amylases, hydrolases, and other proteases), fabric softeners, polymeric soil release agents, polymeric dispersing agents, and suds suppressors. The compositions herein may further include one or more other detergent adjunct materials or other materials for assisting or enhancing cleaning performance, treatment of the substrate to be cleaned, or to modify the aesthetics of the detergent composition (e.g., perfumes, colorants, dyes, etc.). The detergent compositions herein may further comprise other known detergent cleaning components including alkoxylated polycarboxylates, bleaching compounds, brighteners, chelating agents, clay soil removal/antiredeposition agents, dye transfer inhibiting agents, enzymes, enzyme stabilizing systems, fabric softeners, polymeric soil release agents, polymeric dispersing agents, suds suppressors. The detergent composition may also comprise other ingredients including carriers, hydrotropes, processing aids, dyes or pigments, solvents for liquid formulations, solid fillers for bar compositions.

Method of Treating or Preventing Skin Flaking

Another aspect of the present invention relates to a method of treating or preventing skin flaking. The method comprises topical application of a safe and effective amount of a composition comprising the protease EOS.

Herein, "safe and effective amount" means an amount of protease EOS high enough to provide a significant positive modification of the condition to be treated, but low enough to avoid serious side effects (at a reasonable benefit/risk ratio), within the scope of sound medical judgment. A safe and effective amount of protease EOS will vary with the particular condition being treated, the age and physical condition of the subject being treated, the severity of the condition, the duration of the treatment, the nature of concurrent therapy and like factors.

Suitable compositions for use in the subject method include the above-described skin care compositions, including hair care compositions (for example, treating/preventing dandruff caused by skin flaking.

The following examples illustrate the present invention without, however, limiting the same thereto.

EXAMPLE 1

Plasmid Manipulations

All molecular biological methods were in accordance with those previously described (Maniatis et al. (1989). 1–1626). oligonucleotides were purchased from Ransom Hill Biosciences (Ransom Hill, Calif.) and all restriction endonucleases and other DNA modifying enzymes were from New England Biolabs (Beverly, Mass.) unless otherwise specified. The protease EOS expression construct was made in the baculovirus expression vector pFastBacl (Life Technologies, Gaithersberg, Md.) as described below. All construct manipulations were confirmed by dye terminator cycle sequencing using Allied Biosystems 377 fluorescent sequencers (Perkin Elmer, Foster City, Calif.).

Accuisition of Protease EOS cDNA

Eosinophil RNA was isolated from pooled diseased eosinophils obtained from allergic asthmatic individuals. Eosinophils were lysed immediately following collection and purification in a buffer containing guanidinium isothiocyanate. The lysate was spun through CsCl to obtain total RNA, followed by poly A isolation using oligotex latex beads. The cDNA synthesis was initiated using a NotI-oligo(dT) primer and double-stranded cDNA was blunted, ligated to Sal I adaptors, digested with Not I, size-selected, and cloned into the Not I and Sal I sites of the pSPORT1 vector (Life Technologies, Gaithersberg, Md.). A clone, corresponding to the full-length protease EOS cDNA, contained an open reading frame of 855 nucleotides (FIG. 1), and had homology to other S1 serine proteases. This clone is also likely to contain the entire 3' untranslated since an AATAAA motif resides 18 nucleotides upstream of a poly A stretch of 50 nucleotides (in this particular clone, data not shown) a subset of which is presented in FIG. 1. Homology searches of the Genbank database with the protease EOS cDNA indicated that this was a novel cDNA but had identity with the human cosmid clone (407D8, Genbank accession # AC005570), which maps to chromosome 16p13.3, indicating the position of protease EOS gene. The deduced open reading frame encodes a preproEOS protein of 284 amino acids (FIG. 1), with an estimated molecular mass ($M_r$) of about 30-Kd, and a strong homology to other serine proteases. The catalytic triad residues H, D and S are located at positions 77, 126 and 231, respectively. The zymogen activation sequence MSSR-IVGG (positions 33 to 40) is very similar to that of other S1 serine proteases and predicts a mature protein of 284 amino acids. A signal peptide of 22 amino acids is predicted by statistical method (Von Heijne (1986). *Nucleic Acids Res.* 14:4683–90) indicating a pro peptide of 14 amino acids. FASTA homology against the SWISS-PROT database indicates that the top match to protease EOS is the human prostasin precursor EC 3.4.21 SW:Q16651 (Yu et al. (1995). *J. Biol. Chem.* 270:13483–9; Yu et al. (1996). *Genomics* 32:334–40) (47.1% identity in 276 aa. overlap). The next match is dog tryptase precursor EC 3.4.21.59 SW:P15944 (Vanderslice et al. (1989). *Biochemistry* 28:4148–55) (48.2% identity in 274 aa. overlap). The next match corresponding to a known protein is human beta-tryptase precursor; tryptase 2 EC 3.4.21.59 SW:P20231 (Miller et al. (1990). *J. Clin. Invest.* 86:864–700) (44.3% identity in 273 aa. overlap). A phylogenetic tree of an alignment of the deduced protease EOS amino acid sequence with other members of the S1 serine protease family is shown in FIG. 2 as determined using the MegAlign 3.1.7 program (DNASTAR Inc., Madison, Wis.).

EXAMPLE 2

Tissue Distribution of The Protease EOS mRNA

We employed a highly sensitive PCR profiling technique to identify the tissue distribution of protease EOS mRNA. For this application, several human CDNA libraries (all were from Clontech, (Palo Alto, Calif.) except the CHRF-288 megakaryocytic cell line and human gel filtered platelet libraries which we constructed using the ZAP Express cDNA system (Stratagene, La Jolla, Calif.). The PCR primers for the profiling analysis were as follows:

SEQ.ID.NO.:2: 5'-GAGAAAGTCAGATTCACAGC-3'
SEQ.ID.NO.:3: 5'-CTGCTTAGGGTCTCTTTAGG-3'

Figure 3:
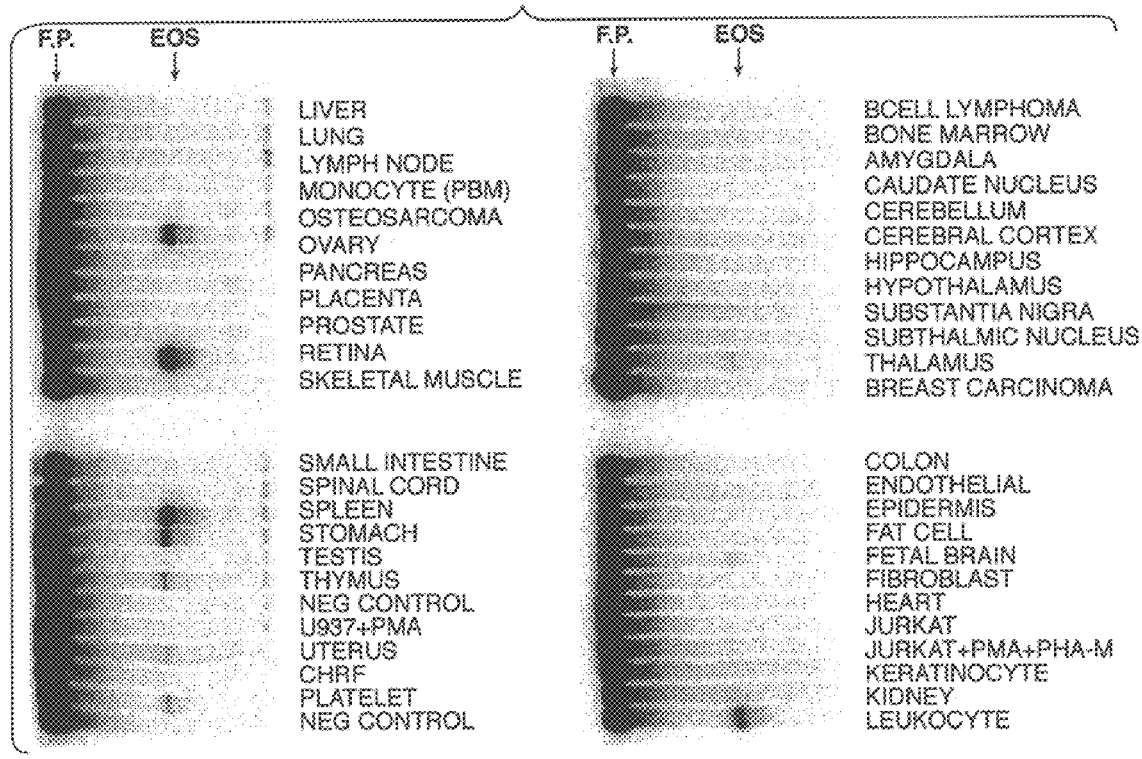
FIG. 3—PCR-based tissue distribution indicates that the protease EOS mRNA is restricted. Autoradiograms of gels are shown with the position of the EOS specific PCR product (EOS), as detected by the hybridization of a labeled nested probe, which was resolved following electrophoresis from the free probe (F.P.). The cDNA libraries of tissues and cell lines analyzed are as indicated.

Briefly, the 50 l PCR reactions used 1 l of diluted phage stock (~$10^8$ to $10^{10}$ pfu/ml) from each of the cDNA libraries tested. Reactions were initially denatured at 94° C. for 5 minutes and subjected to 35 cycles of 94° C. for 20 seconds; 56° C. for 20 seconds; and then 72° C. for 30 seconds followed by a final 72° C. elongation for 10 minutes A nested primer probe of the sequence SEQ.ID.NO.:4: 5'-TGAGCGGCCTTTAAGAGTTGAGAGACAGCCGG CAGGGAAT-3 was radiolabeled using gamma $^{32}$P-ATP and T4 polynucleotide kinase (Life Technologies, Gaithersberg, Md.) and unincorporated label was removed, following the reaction, using a QIAquick nucleotide removal column (Qiagen, Valencia, Calif.). The $^{32}$P end-labeled nested primer probe ($1 \times 10^5$ cpm) was combined with 10 l of each sample following the PCR reaction. The PCR product-probe mixtures were denatured at 94° C. for 5 minutes; hybridized at 60° C. for 15 minutes, and cooled to 4° C. The annealed samples (10 l) were electrophoresed in 6% Tris-Borate-EDTA non-denaturing polyacrylamide gels (Novex), dried and exposed by autoradiography. A PCR profile of the cDNA libraries used in FIG. 3 with beta-actin PCR primers and labeled nested primer probe produced a beta-actin PCR product in all samples examined As seen in FIG. 3, the distribution of protease EOS mRNA is highly restricted to specific tissues and cell types. The tissue types expressing the protease EOS transcript are retina, ovary, and spleen, stomach, and to a lesser extent thymus, uterus and thalamus. Of particular significance is that EOS protease MRNA is not expressed in pancreas, liver or prostate, tissues normally found to express numerous serine protease genes. It is of interest that we detect the protease EOS PCR product in cDNA libraries constructed from human gel filtered platelets. This strongly suggests that protease EOS is expressed in human platelets. The platelets used to construct the cDNA library analyzed in the PCR tissue profile of FIG. 3 contained extremely low levels of contaminating erythrocytes and other blood cells (<1 per $10^6$ platelets), so we can not rule out the possibility of leukocyte contamination, which would generate a false positive signal in this sensitive PCR assay. Cell localization by in situ hybridization or sensitive in situ PCR, and confirmation with protease EOS specific antisera, could be employed to address this issue.

EXAMPLE 3

Construct Generation For The Expression of Active Protease EOS

Since members of the S1 protease family are most often synthesized as inactive zymogen precursors, and require limited proteolysis to become proteolytically active, we have developed a zymogen activation construct to express and permit the generic activation of heterologous serine protease cDNAs. This construct features a bovine preprolactin signal sequence fused in-frame with the MoAb M2 anti-FLAG antibody epitope as previously described (Ishii et al. (1993). *J. Biol. Chem.* 268:9780–6) for the purposes of secretion and antibody detection respectively (PF). Significantly, this construct also contains the enterokinase cleavage site from human trypsinogen I (EK) fused in-frame and downstream from the signal sequence. At the C-terminus, preceding a stop codon, are additional sequences encoding the hemagglutinin (HA) epitope and 6 histidine (6XHIS) codons for detection with the anti-HA antibody MoAb 12 CA5 (Boehringer Mannheim Corp., Indianapolis, Ind.) and affinity purification on nickel resins respectively. A unique Xba I restriction enzyme site, immediately upstream of the epitope/affinity tag sequence and downstream of the PFEK prepro sequence described above, and is the point of in-frame insertion of the catalytic domain of a heterologous serine protease cDNA (FIG. 4). The zymogen activation vector described above has been cloned into a modified pFastBacl transplacement plasmid to generate PFEK-HA6XHIS-TAG FB.

The purified plasmid DNA of the full length protease EOS cDNA was used as a template in a 100 l preparative PCR reaction using the Advantage-GC cDNA Polymerase Mix (Clontech, Palo Alto, Calif.) in accordance with the manufacturer's recommendations. The primers used SEQ.ID.NO.:5: EOS Xba-U 5'-GGGATCTAG AGGACGGAGAGTGGCCGTGGC-3'

SEQ.ID.NO.:7: EOS Xba-L 5'-CTCATCTAGA AGCATTAGAAGTGACGCGAGCCTG-3' contained Xba I cleavable ends, and were designed to flank the catalytic domain of the protease EOS and generate the protease EOS Xba I catalytic cassette. The preparative PCR reaction was run at 18 cycles of 94 ° C. for 30 seconds; 68° C. for 2.5 minutes.

The preparative PCR product was phenol/$CHCl_3$ (1:1) extracted once, $CHCl_3$ extracted, and then EtOH precipitated with glycogen (Boehringer Mannheim Corp., Indianapolis, Ind.) and carrier. The precipitated pellet was rinsed with 70% EtOH, dried by vacuum, and resuspended in 80 μl $H_2O$, 10 μl restriction buffer number 2 and 1 μl 100xBSA (New England Biolabs, Beverly, Mass.). The product was digested for 3 hr. at 37° C. with 200 units Xba I restriction enzyme (New England Biolabs, Beverly, Mass.). The Xba I digested product was phenol/$CHCl_3$ (1:1) extracted once, $CHCl_3$ extracted, EtOH precipitated, rinsed with 70% EtOH, and dried by vacuum. For purification from contaminating template plasmid DNA, the product was electrophoresed through 1.0% low melting temperature agarose (Life Technologies, Gaithersberg, Md.) gels in TAE buffer (40 mM Tris-Acetate, 1 mM EDTA pH 8.3) and excised from the gel. An aliquot of the excised product was then used for in-gel ligations with the Xba I digested, dephosphorylated and gel purified, zymogen activation vector described above. Clones containing the EOS Xba cassette, inserted in the correct orientation to generate the construct PFEK-protease EOS-HA6XHIS-TAG 64, were confirmed by sequence analyses to ensure that the proper translational register with respect to the $NH_2$-terminal PFEK prepro sequence and C-terminal HA6XHIS epitope/affinity tag was maintained.

EXAMPLE 4

Expression of Recombinant Protease EOS

The recombinant bacmid containing the PFEK-protease EOS-HA6XHIS construct was prepared from bacterial transformation, selection, growth, purification and PCR confirmation in accordance with the manufacturer's recommendations. Cultured Sf9 insect cells (ATCC CRL-1711) were transfected with purified bacmid DNA and several days later, conditioned media containing recombinant PFEK-EOS-HA6XHIS baculovirus was collected for viral stock amplification. Sf9 cells growing in Sf-900 II SFM at a density of $2 \times 10^6$/ml were infected at a multiplicity of infection of 2 at 27° C. for 80 hours, and cell pellets were collected for purification of PFEK-EOS-HA6XHIS.

EXAMPLE 5

Purification, and Activation of Recombinant Protease EOS

Figure 6:
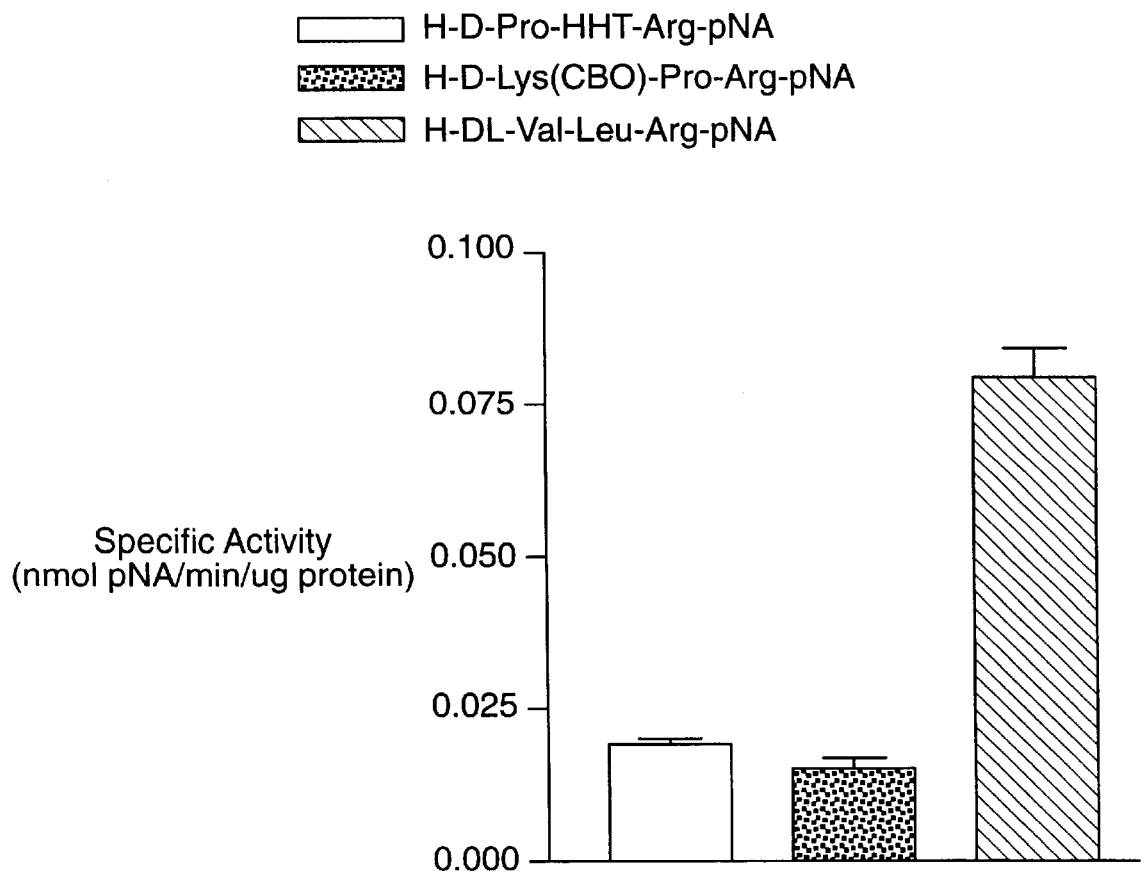
FIG. 6—Functional amidolytic activities of the recombinant protease EOS-HA6XHIS expressed, purified and activated from the activation construct were determined using chromogenic substrates.

Cells were lyzed on ice in 20 mM Tris (pH7.4), 150 mM NaCl, 1% Triton X-100, 1 mM EDTA, 1 mM EGTA, 1 mM PMSF, leupeptin (1 g/ml), and pepstatin (1 g/ml). Cell lysates were mixed with anti-FLAG M2 affinity gel (Eastman Kodak Co., New Haven, Conn.) and bound at 4° C. for 3 hours with gentle rotation. The zymogen-bound resin was washed 3 times with TBS buffer (50 mM Tris-HCl, 150 mM NaCl at a final pH of 7.5), and eluted by competition with FLAG peptide (100 g/ml) in TBS buffer. The eluted zymogen was dialyzed overnight against TBS in Spectra/Por membrane (MWCO: 12,000–14,000) (Spectra Medical Industries, Inc., Huston, Tex.). Ni-NTA (150 l of a 50% slurry/per 100 g of zymogen) (Qiagen, Valencia, Calif.) was added to 5 ml the dialyzed sample and mixed by shaking at 4° C. for 60 minutes The zymogen-bound resin was washed 3 times with wash buffer [10 mM Tris-HCl (pH 8.0), 300 mM NaCl, and 15 mM imidazole], followed by with a 1.5 ml wash with ds $H_2O$. Zymogen cleavage was carried out by adding enterokinase (10 U per 50 g of zymogen) (Novagen, Inc., Madison Wis.; or Sigma, St. Louis, Mo.) to the zymogen-bound Ni-NTA beads in a small volume at room temperature overnight with gentle shaking in a buffer containing 20 mM Tris-HCl (pH 7.4), 50 mM NaCl, and 2.0 mM $CaCl_2$. The resin was then washed twice with 1.5 ml wash buffer. The activated protease EOS-HA6XHIS was eluted with elution buffer [20 mM Tris-HCl (pH 7.8), 250 mM NaCl, and 250 mM imidazole]. Eluted protein concentration was determined by a Micro ECA Kit (Pierce, Rockford, Ill.) using bovine serum albumin as a standard. Amidolytic activities of the activated protease EOS-HA6XHIS was monitored by release of para-nitroaniline (pNA) from the synthetic substrates indicated in FIG. 6. The chromogenic substrates used in these studies were all commercially available (Bachem California Inc., Torrance, Pa.; American Diagnostica Inc., Greenwich, Conn.; Kabi Pharmacia Hepar Inc., Franklin, Ohio). Assay mixtures contained chromogenic substrates at 500 $\mu$M and 10 mM Tris-HCl (pH 7.8), 25 mM NaCl, and 25 mM imidazole. Release of pNA was measured over 120 minutes at 37° C. on a micro-plate reader (Molecular Devices, Menlo Park, Calif.) with a 405 nm absorbance filter. The initial reaction rates (Vmax, mOD/min) were determined from plots of absorbance versus time using Softmax (Molecular Devices, Menlo Park, Calif.). The specific activities (nmole pNA produced /min/ug protein) of the activated protease EOS-HA6XHIS for the various substrates are presented in FIG. 6. No measurable chromogenic amidolytic activity was detected with the purified unactivated PFEK-protease EOS-HA6XHIS zymogen.

Electrophoresis and Western Blotting Detection of Recombinant Proteases EOS

Samples of the purified PFEK-protease EOS-HAGXHIS zymogen or activated protease EOS-HA6XHIS, denatured in the presence of the reducing agent dithiothreitol (DTT), were analyzed by SDS-Pa.GE (Bio Rad, Hercules Calif.) stained with Coomassie Brilliant Blue. For Western blotting, gels were electrotransfer to Hybond ECL membranes (Amersham, Arlington Heights, Ill.). The FLAG-tagged PFEK-protease EOS-HA6XHIS zymogen expressed from infected Sf9 cells was detected with anti-Flag M2 antibody (Eastman Kodak Co., New Haven, Conn.). The secondary antibody was a goat-anti-mouse IgG (H+L), horseradish peroxidase-linked F(ab')2 fragment, (Boehringer Mannheim Corp., Indianapolis, Ind.) and was detected by the ECL kit (Amersham, Arlington Heights, Ill.).

EXAMPLE 6

Chromogenic Assay

Amidolytic activities of the activated serine proteases are monitored by release of para-nitroaniline (pNA) from synthetic substrates that are commercially available (Bachem California Inc., Torrance, Pa.; American Diagnostica Inc., Greenwich, Conn.; Kabi Pharmacia Hepar Inc., Franklin, Ohio). Assay mixtures contain chromogenic substrates in 500 $\mu$M and 10 mM TRIS-HCl (pH 7.8), 25 mM NaCl, and 25 mM imidazole. Release of pNA is measured over 120 min at 37° C. on a micro-plate reader (Molecular Devices, Menlo Park, Calif.) with a 405 nm absorbance filter. The initial reaction rates (Vmax, mOD/min) are determined from plots of absorbance versus time using Softmax (Molecular Devices, Menlo Park, Calif.). Compounds that modulate a serine protease of the present invention are identified through screening for the acceleration, or more commonly, the inhibition of the proteolytic activity. Although in the present case chromogenic activity is monitored by an increase in absorbance, fluorogenic assays or other methods such as FRET to measure proteolytic activity as mentioned above, can be employed. Compounds are dissolved in an appropriate solvent, such as DMF, DMSO, methanol, and diluted in water to a range of concentrations usually not exceeding 100 $\mu$M and are typically tested, though not limited to, a concentration of 1000-fold the concentration of protease. The compounds are then mixed with the protein stock solution, prior to addition to the reaction mixture. Alternatively, the protein and compound solutions may be added independently to the reaction mixture, with the compound being added either prior to, or immediately after, the addition of the protease protein References Cited Abu-Ghazaleh, R. I., Kita, H., and Gleich, G. J. (1992). Eosinophil activation and function in health and disease. Immunol. Ser. 57, 137–67.

Altschul, S. F., Gish, W., Miller, W., Myers, E. W., and Lipman, D. J. (1990). Basic local alignment search tool. J. Mol. Biol. 215, 403–10.

Buroker-Kilgore, M., and Wang, K. K. W. (1993). A Coomassie Brilliant Blue G-250-based calorimetric assay for measuring activity of calpain and other proteases. Anal. Biochem. 208, 387–92.

Caughey, G. H. (1995). Mast cell chymases and tryptases: Phylogeny, family relations, and biogenesis. In Clin. Allergy Immunol., pp. 305–29.

Coolican, S. A., Haiech, J., and Hathaway, D. R. (1986). The role of subunit autolysis in activation of smooth muscle calcium-dependent proteases. J. Biol. Chem. 261, 4170–6.

Daniels, S. E., Bhattacharrya, S., James, A., Leaves, N. I., Young, A., Hill, M. R., Faux, J. A., Ryan, G. F., le Souef, P. N., and et al. (1996). A genome-wide search for quantitative trait loci underlying asthma. Nature (London) 383, 247–253.

Davie, E. W., Fujikawa, K., and Kisiel, W. (1991). The coagulation cascade: initiation, maintenance, and regulation. Biochemistry 30, 10363–70.

Emi, M., Nakamura, Y., Ogawa, M., Yamamoto, T., Nishide, T., Mori, T., and Matsubara, K. (1986). Cloning, characterization and nucleotide sequences of two cDNAs encoding human pancreatic trypsinogens. Gene 41, 305–10.

Fukushima, D., Kitamura, N., and Nakanishi, S. (1985). Nucleotide sequence of cloned cDNA for human pancreatic kallikrein. Biochemistry 24, 8037–43.

Gleich, G. J. (1996). Eosinophil granule proteins and bronchial asthma. Allergol. Int. 45, 35–44.

Gleich, G. J., Adolphson, C. R., and Leiferman, K. M. (1993). The biology of the eosinophilic leukocyte. In Annu. Rev. Med., pp. 85–101.

Hansson, L., Stroemqvist, M., Baeckman, A., Wallbrandt, P., Carlstein, A., and Egelrud, T. (1994). Cloning, expression, and characterization of stratum corneum chymotryptic enzyme. A skin-specific human serine proteinase. J. Biol. Chem. 269, 19420–6.

Higgins, D. G., and Sharp, P. M. (1989). Fast and sensitive multiple sequence alignments on a microcomputer. Comput. Appl. Biosci. 5, 151–3.

Ishii, K., Hein, L., Kobilka, B., and Coughlin, S. R. (1993). Kinetics of thrombin receptor cleavage on intact cells. Relation to signaling. J. Biol. Chem. 268, 9780–6.

Johnson, P. R. A., Ammit, A. J., Carlin, S. M., Armour, C. L., Caughey, G. H., and Black, J. L. (1997). Mast cell tryptase potentiates histamine-induced contraction in human sensitized bronchus. Eur. Respir. J. 10, 38–43.

Katunuma, N., and Kido, H. (1988). Biological functions of serine proteases in mast cells in allergic inflammation. In J. Cell. Biochem., pp. 291–301.

Kohler, G., and Milstein, C. (1976). Derivation of specific antibody-producing tissue culture and tumor lines by cell fusion. Eur J Immunol 6, 511–9.

Little, S. P., Dixon, E. P., Norris, F., Buckley, W., Becker, G. W., Johnson, M., Dobbins, J. R., Wyrick, T., Miller, J. R., Mackellar, W., Hepburn, D., Corvalan, J., Mcclure, D., Liu, X., Stephenson, D., Clemens, J., and Johnstone, E. M. (1997). Zyme, a novel and potentially amyloidogenic enzyme cDNA isolated from Alzheimer's disease brain. J. Biol. Chem. 272, 25135–25142.

Lonergan, S. M., Johnson, M. H., and Calkins, C. R. (1995). Improved calpain assay using fluorescein isothiocyanate-labeled casein. J. Food Sci. 60, 72–3, 78.

Maniatis, T., Fritsch, E. F., and Sambrook, J. (1989). Molecular Cloning: A Laboratory Manual, 2nd ed.: Cold Spring Harbor Laboratory, Cold Spring Harbor, N.Y.

Miller, J. S., Moxley, G., and Schwartz, L. B. (1990). Cloning and characterization of a second complementary DNA for human tryptase. J. Clin. Invest. 86, 864–700.

Ng, M., and Auld, D. S. (1989). A fluorescent oligopeptide energy transfer assay with broad applications for neutral proteases. Anal. Biochem. 183, 50–6.

Pallaoro, M., Fejzo, M. S., Shayesteh, L., Blount, J. L., and Caughey, G. H. (1999). Characterization of genes encoding known and novel human mast cell tryptases on chromosome 16p13.3. J. Biol. Chem. 274, 3355–3362.

Pearson, W. R., and Lipman, D. J. (1988). Improved tools for biological sequence comparison. Proc. Natl. Acad. Sci. U. S. A. 85, 2444–8.

Pham, C. T. N., Thomas, D. A., Mercer, J. D., and Ley, T. J. (1998). Production of fully active recombinant murine granzyme B in yeast. J. Biol. Chem. 273, 1629–1633.

Proud, D., and Kaplan, A. P. (1988). Kinin formation: mechanisms and role in inflammatory disorders. Annu. Rev. Immunol. 6, 49–83.

Rawlings, N. D., and Barrett, A. J. (1994). Families of serine peptidases. Methods Enzymol. 244, 19–61.

Reid, K. B. M., and Porter, R. R. (1981). The proteolytic activation systems of complement. Annual Review of Biochemistry 50, 433–464.

Saitou, N., and Nei, M. (1987). The neighbor-joining method: a new method for reconstructing phylogenetic trees. Mol Biol Evol 4, 406–25.

Simon, S. R. (1993). Oxidants, metalloproteases and serine proteases in inflammation. In Agents Actions Suppl., pp. 27–37.

Smyth, M. J., O° Connor, M. D., and Trapani, J. A. (1996). Granzymes: a variety of serine protease specif icities encoded by genetically distinct subfamilies. In J. Leukocyte Biol., pp. 555–562.

Takayama, T. K., Fujikawa, K., and Davie, E. W. (1997). Characterization of the precursor of prostate-specific antigen Activation by trypsin and by human glandular kallikrein. J. Biol. Chem. 272, 21582–21588.

Tomita, N., Izumoto, Y., Horii, A., Doi, S., Yokouchi, H., Ogawa, M., Mori, T., and Matsubara, K. (1989). Molecular cloning and nucleotide sequence of human pancreatic prechymotrypsinogen CDNA. Biochem. Biophys. Res. Commun. 158, 569–75.

Twining, S. S. (1984). Fluorescein isothiocyanate-labeled casein assay for proteolytic enzymes. Anal. Biochem. 143, 30–4.

Vanderslice, P., Craik, C. S., Nadel, J. A., and Caughey, G. H. (1989). Molecular cloning of dog mast cell tryptase and a related protease: structural evidence of a unique mode of serine protease activation. Biochemistry 28, 4148–55.

Von Heijne, G. (1986). A new method for predicting signal sequence cleavage sites. Nucleic Acids Res. 14, 4683–90.

Wadstroem, T., and Smyth, C. J. (1973). Zymogram methods applied to thin-layer isoelectric focusing in polyacrylamide gel. In Sci. Tools, pp. 17–21.

Wang, Z.-m., Rubin, H., and Schechter, N. M. (1995). Production of active recombinant human chymase from a construct containing the enterokinase cleavage site of trypsinogen in place of the native propeptide sequence. Biol. Chem. Hoppe-Seyler 376, 681–4.

Yamaoka, K., Masuda, K.-i., Ogawa, h., Takagi, K.-i., Umemoto, N., and Yasuoka, S. (1998). Cloning and characterization of the cDNA for human airway trypsin-like protease. J. Biol. Chem. 273, 11895–11901.

Yamashiro, K., Tsuruoka, N., Kodama, S., Tsujimoto, M., Yamamura, Y., Tanaka, T., Nakazato, H., and Yamaguchi, N. (1997). Molecular cloning of a novel trypsin-like serine protease (neurosin) preferentially expressed in brain. Biochim. Biophys. Acta 1350, 11–14.

Yu, J. X., Chao, L., and Chao, J. (1995). Molecular cloning, tissue-specific expression, and cellular localization of human prostasin MRNA. J. Biol. Chem. 270, 13483–9.

Yu, J. X., Chao, L., Ward, D. C., and Chao, J. (1996). Structure and chromosomal localization of the human prostasin (PRSS8) gene. Genomics 32, 334–40.

What is claimed is:

1. An isolated protein having an amino acid sequence selected from a group consisting of an amino acid sequence set forth in SEQ ID NO: 7 and an amino acid sequence set forth in SEQ ID NO: 9.

2. A pharmaceutical composition comprising the protein of claim 1.

3. The pharmaceutical composition of claim 2 wherein said composition is a topical skin care composition.

4. A method of treating an imbalance of desquamation comprising topical application of the composition of claim 3.

5. A kit comprising a serine protease EOS protein having an amino acid sequence selected from a group consisting of an amino acid sequence set forth in SEQ ID NO:7 and an amino acid sequence set forth in SEQ ID NO: 9.

* * * * *